(12) United States Patent
Shih et al.

(10) Patent No.: US 9,771,589 B2
(45) Date of Patent: Sep. 26, 2017

(54) TREATING HEPATITIS VIRUS INFECTION BY MODULATING MICRORNAS MIR-130A, MIR-130B, MIR-204, OR MIR-1236

(71) Applicant: Academia Sinica, Taipei (TW)

(72) Inventors: Chiaho Shih, Houston, TX (US); Jyun-Yuan Huang, Kaohsiung (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/023,284

(22) PCT Filed: Sep. 19, 2014

(86) PCT No.: PCT/US2014/056586
§ 371 (c)(1),
(2) Date: Mar. 18, 2016

(87) PCT Pub. No.: WO2015/042420
PCT Pub. Date: Mar. 26, 2015

(65) Prior Publication Data
US 2016/0251661 A1 Sep. 1, 2016

Related U.S. Application Data

(60) Provisional application No. 61/880,508, filed on Sep. 20, 2013.

(51) Int. Cl.
| | | |
|---|---|---|
| C12N 15/113 | (2010.01) |
| C12N 7/00 | (2006.01) |
| A61K 31/7088 | (2006.01) |
| A61K 45/06 | (2006.01) |

(52) U.S. Cl.
CPC ...... *C12N 15/1131* (2013.01); *A61K 31/7088* (2013.01); *A61K 45/06* (2013.01); *C12N 7/00* (2013.01); *C12N 15/113* (2013.01); *C12N 2310/113* (2013.01); *C12N 2310/141* (2013.01); *C12N 2310/531* (2013.01); *C12N 2320/30* (2013.01); *C12N 2730/10111* (2013.01)

(58) Field of Classification Search
None
See application file for complete search history.

(56) References Cited

FOREIGN PATENT DOCUMENTS

| CN | 101368213 A | 2/2009 |
| WO | WO-2012/135817 A2 | 10/2012 |

OTHER PUBLICATIONS

Tang et al "The Hepatitis B Virus-Associated Estrogen Receptor Alpha (ERα) was Regulated by MicroRNA-130a in HepG2.2.15 Human Hepatocellular Carcinoma Cells" Acta Biochimica et Biophysica Sinica vol. 43, pp. 640-646, 2011.
Xu et al "Hepatitis B Virus X Protein Represses miRNA-148a to Enhance Tumorigenesis" The Journal of Clinical Investigation vol. 123, pp. 630-645, 2013.
Ye et al "Disruption of Hepatitis C Virus RNA Replication Through Inhibition of Host Protein Geranylgeranylation" PNAS vol. 100, pp. 15865-15870, 2003.

*Primary Examiner* — Jennifer McDonald
(74) *Attorney, Agent, or Firm* — Cesari and McKenna, LLP

(57) ABSTRACT

Methods and pharmaceutical compositions for regulating hepatitis virus replication, involving a miR-130a RNA, a miR-130b RNA, a miR-204 RNA, a miR-1236 RNA, or a combination thereof.

18 Claims, 50 Drawing Sheets

|  | HBV DNA | HBV RNA | HBV protein | 3' UTR reporter assay |
|---|---|---|---|---|
| miR-1236: | + | – | + | + |
| miR-130a: | + | + | + | – |
| miR-204: | + | – | – | – |

"+" detectable anti-HBV effect
"–" no detectable anti-HBV effect

B

C

D

E

F

G

H

I

J

K

L

M

O

P

S

HepG2

T

HepG2

U

V

W

X

Y

Z

A

C

D

E

A

B

C

D

E

G

F

H

I

J

K

L

M

O

P

A

B

C

A

B

C

E.

D

F

G

H

I

A

B

A

B

C

D

SEQUENCE LISTING

<160> NUMBER OF SEQ ID NOS: 75

<210> SEQ ID NO 1
<211> LENGTH: 22
<212> TYPE: RNA
<213> ORGANISM: Artificial Sequence
<220> FEATURE:
<223> OTHER INFORMATION: Synthetic Polypeptide

<400> SEQUENCE: 1
cagugcaaug uuaaaagggc au          22

```
<210> SEQ ID NO 2
<211> LENGTH: 22
<212> TYPE: RNA
<213> ORGANISM: Artificial Sequence
<220> FEATURE:
<223> OTHER INFORMATION: Synthetic Polypeptide

<400> SEQUENCE: 2
cagugcaaug augaaagggc au                                              22

<210> SEQ ID NO 3
<211> LENGTH: 22
<212> TYPE: RNA
<213> ORGANISM: Artificial Sequence
<220> FEATURE:
<223> OTHER INFORMATION: Synthetic Polypeptide

<400> SEQUENCE: 3
uucccuuugu cauccaugc cu                                               22

<210> SEQ ID NO 4
<211> LENGTH: 22
<212> TYPE: RNA
<213> ORGANISM: Artificial Sequence
<220> FEATURE:
<223> OTHER INFORMATION: Synthetic Polypeptide

<400> SEQUENCE: 4 ccucuuccec uugucucucc ag                                              22

<210> SEQ ID NO 5
<211> LENGTH: 22
<212> TYPE: RNA
<213> ORGANISM: Artificial Sequence
<220> FEATURE:
<223> OTHER INFORMATION: Synthetic Polypeptide

<400> SEQUENCE: 5
ugggaggagu uggggggagga ga                                             22

<210> SEQ ID NO 6
<211> LENGTH: 22
<212> TYPE: RNA
<213> ORGANISM: Artificial Sequence
<220> FEATURE:
<223> OTHER INFORMATION: Synthetic Polypeptide

<400> SEQUENCE: 6
cuucuucucc uugucucucc ag                                              22

<210> SEQ ID NO 7
<211> LENGTH: 22
<212> TYPE: RNA
<213> ORGANISM: Artificial Sequence
<220> FEATURE:
<223> OTHER INFORMATION: Synthetic Polypeptide

<400> SEQUENCE: 7
ugggaggagu ugggagagga aa                                              22

<210> SEQ ID NO 8
<211> LENGTH: 23
<212> TYPE: RNA
<213> ORGANISM: Artificial Sequence
<220> FEATURE:
<223> OTHER INFORMATION: Synthetic Polypeptide
```

```
<400> SEQUENCE: 8
aagcaguguu ucuacuugca cua                                               23

<210> SEQ ID NO 9
<211> LENGTH: 22
<212> TYPE: RNA
<213> ORGANISM: Artificial Sequence
<220> FEATURE:
<223> OTHER INFORMATION: Synthetic Polypeptide

<400> SEQUENCE: 9
cugagcaaug uuaaaagggc au                                                22

<210> SEQ ID NO 10
<211> LENGTH: 23
<212> TYPE: RNA
<213> ORGANISM: Artificial Sequence
<220> FEATURE:
<223> OTHER INFORMATION: Synthetic Polypeptide

<400> SEQUENCE: 10
aagcaguguu ucuacuugcu caa                                               23

<210> SEQ ID NO 11
<211> LENGTH: 89
<212> TYPE: RNA
<213> ORGANISM: Homo sapiens

<400> SEQUENCE: 11
ugcugcuggc cagagcucuu uucacauugu gcuacugucu gcaccuguca cuagcagugc       60
aauguuaaaa gggcauuggc cguguagug                                         89

<210> SEQ ID NO 12
<211> LENGTH: 82
<212> TYPE: RNA
<213> ORGANISM: Homo sapiens

<400> SEQUENCE: 12
ggccugcccg acacucuuuc ccuguugcac uacuauaggc cgcugggaag cagugcaaug       60
augaaagggc aucggucagg uc                                                82

<210> SEQ ID NO 13
<211> LENGTH: 110
<212> TYPE: RNA
<213> ORGANISM: Homo sapiens

<400> SEQUENCE: 13
ggcuacaguc uuucuucaug ugacucgugg acuucccuuu gucauccuau gccugagaau       60
auaugaagga ggcugggaag gcaaagggac guucaauugu caucacuggc                  110

<210> SEQ ID NO 14
<211> LENGTH: 102
<212> TYPE: RNA
<213> ORGANISM: Homo sapiens

<400> SEQUENCE: 14
gugagugaca ggggaaaugg ggauggacug gaagugggca gcauggagcu gaccuucauc       60
auggcuuggc caacauaaug ccucuucccc uugucucucc ag                          102

<210> SEQ ID NO 15
<211> LENGTH: 21
```

```
<212> TYPE: DNA
<213> ORGANISM: Artificial Sequence
<220> FEATURE:
<223> OTHER INFORMATION: Synthetic Polypeptide

<400> SEQUENCE: 15
catcttcaaa agcggacact c                                            21

<210> SEQ ID NO 16
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 16
tcatggaaat ccacatccaa                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 17
ggcaaaagga agagtggtga                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 18
accagggtag ctgactggtg                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 19
agcaggtctg gagcaaacat                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 20
cacccaccca ggtagctaga                                              20

<210> SEQ ID NO 21
<211> LENGTH: 32
<212> TYPE: DNA
<213> ORGANISM: Artificial Sequence
<220> FEATURE:
<223> OTHER INFORMATION: Synthetic Polypeptide

<400> SEQUENCE: 21
```
ggaggagttg ggagaggaaa ttaggttaaa gg          32

<210> SEQ ID NO 22
<211> LENGTH: 32
<212> TYPE: DNA
<213> ORGANISM: Artificial Sequence
<220> FEATURE:
<223> OTHER INFORMATION: Synthetic Polypeptide

<400> SEQUENCE: 22
cctttaacct aatttcctct cccaactcct cc          32

<210> SEQ ID NO 23
<211> LENGTH: 30
<212> TYPE: DNA
<213> ORGANISM: Artificial Sequence
<220> FEATURE:
<223> OTHER INFORMATION: Synthetic Polypeptide

<400> SEQUENCE: 23
atattctaga gcttgttcag cggttctttc            30

<210> SEQ ID NO 24
<211> LENGTH: 30
<212> TYPE: DNA
<213> ORGANISM: Artificial Sequence
<220> FEATURE:
<223> OTHER INFORMATION: Synthetic Polypeptide

<400> SEQUENCE: 24
atattctaga agccatcaag aaaggacaca            30

<210> SEQ ID NO 25
<211> LENGTH: 32
<212> TYPE: DNA
<213> ORGANISM: Artificial Sequence
<220> FEATURE:
<223> OTHER INFORMATION: Synthetic Polypeptide

<400> SEQUENCE: 25
gcagtgtttc tacttgctca agcatggcct ct          32

<210> SEQ ID NO 26
<211> LENGTH: 32
<212> TYPE: DNA
<213> ORGANISM: Artificial Sequence
<220> FEATURE:
<223> OTHER INFORMATION: Synthetic Polypeptide

<400> SEQUENCE: 26
agaggccatg cttgagcaag tagaaacact gc          32

<210> SEQ ID NO 27
<211> LENGTH: 32
<212> TYPE: DNA
<213> ORGANISM: Artificial Sequence
<220> FEATURE:
<223> OTHER INFORMATION: Synthetic Polypeptide

<400> SEQUENCE: 27
gcacctgtca ctagctgagc aatgttaaaa gg          32

<210> SEQ ID NO 28
<211> LENGTH: 32
<212> TYPE: DNA
<213> ORGANISM: Artificial Sequence

```
<220> FEATURE:
<223> OTHER INFORMATION: Synthetic Polypeptide

<400> SEQUENCE: 28
ccttttaaca ttgctcagct agtgacaggt gc                                32

<210> SEQ ID NO 29
<211> LENGTH: 73
<212> TYPE: DNA
<213> ORGANISM: Artificial Sequence
<220> FEATURE:
<223> OTHER INFORMATION: Synthetic Polypeptide

<400> SEQUENCE: 29
gcactgctcg agatgccctt ttaacattgc actggaattc atgcccttt aacattgcac    60 tgctcgagat gcc                                                     73

<210> SEQ ID NO 30
<211> LENGTH: 72
<212> TYPE: DNA
<213> ORGANISM: Artificial Sequence
<220> FEATURE:
<223> OTHER INFORMATION: Synthetic Polypeptide

<400> SEQUENCE: 30
gcatctcgag cagtgcaatg ttaaaagggc atgaattcca gtgcaatgtt aaagggcat    60 ctcgagcagt gc                                                      72

<210> SEQ ID NO 31
<211> LENGTH: 30
<212> TYPE: DNA
<213> ORGANISM: Artificial Sequence
<220> FEATURE:
<223> OTHER INFORMATION: Synthetic Polypeptide

<400> SEQUENCE: 31
atatctcgag agatgcattc acaggggttg                                   30

<210> SEQ ID NO 32
<211> LENGTH: 30
<212> TYPE: DNA
<213> ORGANISM: Artificial Sequence
<220> FEATURE:
<223> OTHER INFORMATION: Synthetic Polypeptide

<400> SEQUENCE: 32
atatctcgag gctcagagca gctaatgaag                                   30

<210> SEQ ID NO 33
<211> LENGTH: 29
<212> TYPE: DNA
<213> ORGANISM: Artificial Sequence
<220> FEATURE:
<223> OTHER INFORMATION: Synthetic Polypeptide

<400> SEQUENCE: 33
atatctcgag cagagagtcc tgagccact                                    29

<210> SEQ ID NO 34
<211> LENGTH: 29
<212> TYPE: DNA
<213> ORGANISM: Artificial Sequence
<220> FEATURE:
<223> OTHER INFORMATION: Synthetic Polypeptide
```

<400> SEQUENCE: 34
atatctcgag gggtgggaaa cacacaaga                              29

<210> SEQ ID NO 35
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 35
ccactgctgg ggattgatgt                                        20

<210> SEQ ID NO 36
<211> LENGTH: 24
<212> TYPE: DNA
<213> ORGANISM: Artificial Sequence
<220> FEATURE:
<223> OTHER INFORMATION: Synthetic Polypeptide

<400> SEQUENCE: 36
gagcttaaca tactcagcat aacg                                   24

<210> SEQ ID NO 37
<211> LENGTH: 21
<212> TYPE: DNA
<213> ORGANISM: Artificial Sequence
<220> FEATURE:
<223> OTHER INFORMATION: Synthetic Polypeptide

<400> SEQUENCE: 37
gcggggcaag gtactactta t                                      21

<210> SEQ ID NO 38
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 38
cgttcttggc gttctcctga                                        20

<210> SEQ ID NO 39
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 39
ggagcgagtt tggttgcact                                        20

<210> SEQ ID NO 40
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 40
gtggcactgg gaacacttca                                        20

<210> SEQ ID NO 41
<211> LENGTH: 20

```
<212> TYPE: DNA
<213> ORGANISM: Artificial Sequence
<220> FEATURE:
<223> OTHER INFORMATION: Synthetic Polypeptide

<400> SEQUENCE: 41
cctgccatgc cacaagattc                                              20

<210> SEQ ID NO 42
<211> LENGTH: 19
<212> TYPE: DNA
<213> ORGANISM: Artificial Sequence
<220> FEATURE:
<223> OTHER INFORMATION: Synthetic Polypeptide

<400> SEQUENCE: 42
tctgcatgcc ccacacaat                                               19

<210> SEQ ID NO 43
<211> LENGTH: 18
<212> TYPE: DNA
<213> ORGANISM: Artificial Sequence
<220> FEATURE:
<223> OTHER INFORMATION: Synthetic Polypeptide

<400> SEQUENCE: 43
ccttccccag gagccgac                                                18

<210> SEQ ID NO 44
<211> LENGTH: 18
<212> TYPE: DNA
<213> ORGANISM: Artificial Sequence
<220> FEATURE:
<223> OTHER INFORMATION: Synthetic Polypeptide

<400> SEQUENCE: 44
gctctgtctc caccgctt                                                18

<210> SEQ ID NO 45
<211> LENGTH: 22
<212> TYPE: DNA
<213> ORGANISM: Artificial Sequence
<220> FEATURE:
<223> OTHER INFORMATION: Synthetic Polypeptide

<400> SEQUENCE: 45
tacatggagg agatgcagaa tg                                           22

<210> SEQ ID NO 46
<211> LENGTH: 22
<212> TYPE: DNA
<213> ORGANISM: Artificial Sequence
<220> FEATURE:
<223> OTHER INFORMATION: Synthetic Polypeptide

<400> SEQUENCE: 46
acttgccacc tatgagcttc tc                                           22

<210> SEQ ID NO 47
<211> LENGTH: 22
<212> TYPE: DNA
<213> ORGANISM: Artificial Sequence
<220> FEATURE:
<223> OTHER INFORMATION: Synthetic Polypeptide

<400> SEQUENCE: 47
```
gagatcccag cagagaaggt tt                                                22

<210> SEQ ID NO 48
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 48
agtctcccct gacagcatga                                                   20

<210> SEQ ID NO 49
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 49
cataaagtcc ttcccgctga                                                   20

<210> SEQ ID NO 50
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 50
tctgtgatct cctgcacagc                                                   20

<210> SEQ ID NO 51
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 51
acctcatcat ggcctcactt                                                   20

<210> SEQ ID NO 52
<211> LENGTH: 19
<212> TYPE: DNA
<213> ORGANISM: Artificial Sequence
<220> FEATURE:
<223> OTHER INFORMATION: Synthetic Polypeptide

<400> SEQUENCE: 52
gttgatgacc ggcacactc                                                    19

<210> SEQ ID NO 53
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 53
gagctgcaga tcgatgacaa                                                   20

<210> SEQ ID NO 54
<211> LENGTH: 20
<212> TYPE: DNA
<213> ORGANISM: Artificial Sequence

```
<220> FEATURE:
<223> OTHER INFORMATION: Synthetic Polypeptide

<400> SEQUENCE: 54
tactggcggt cgttgatgta                                                     20

<210> SEQ ID NO 55
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 55
cctctcagga aaggccagta                                                     20

<210> SEQ ID NO 56
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 56
cacttgatcg ttcaggtcca                                                     20

<210> SEQ ID NO 57
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 57
ggagaacagc ccatacctga                                                     20

<210> SEQ ID NO 58
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 58
gcccatccaa tgataaccac                                                     20

<210> SEQ ID NO 59
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 59
gacaagcaca gcgacgagta                                                     20

<210> SEQ ID NO 60
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 60
agctgctcca ccttcttctg                                                     20
```

<210> SEQ ID NO 61
<211> LENGTH: 18
<212> TYPE: DNA
<213> ORGANISM: Artificial Sequence
<220> FEATURE:
<223> OTHER INFORMATION: Synthetic Polypeptide

<400> SEQUENCE: 61
cagaccacca tgcacctg                                                     18

<210> SEQ ID NO 62
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 62
ctcgttgctg ttcttgtcca                                                   20

<210> SEQ ID NO 63
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 63
gcacctgccc ctactgtaaa                                                   20

<210> SEQ ID NO 64
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 64
gcgtttccca cagtatgacc                                                   20

<210> SEQ ID NO 65
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 65
tggctaccct ctgtgacctc                                                   20

<210> SEQ ID NO 66
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 66
cccctcttca tccaggacta                                                   20

<210> SEQ ID NO 67
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 67
atcctcgacc acatttaccg                                               20

<210> SEQ ID NO 68
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 68
tgccactaac tcctgtgcat                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 69
tatcagcacg agaggctgaa                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 70
tcaaaacggt ccctcagttc                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 71
gcaaacaccc agctgtcaaa                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 72
gcacatcatc agcaagccag                                               20

<210> SEQ ID NO 73
<211> LENGTH: 18
<212> TYPE: DNA
<213> ORGANISM: Artificial Sequence
<220> FEATURE:
<223> OTHER INFORMATION: Synthetic Polypeptide

<400> SEQUENCE: 73
gagtgggctg cagtgaca                                                 18

<210> SEQ ID NO 74

```
<211> LENGTH: 20
<212> TYPE: DNA
<213> ORGANISM: Artificial Sequence
<220> FEATURE:
<223> OTHER INFORMATION: Synthetic Polypeptide

<400> SEQUENCE: 74
gcacgtactg tcggaagtca                                              20

<210> SEQ ID NO 75
<211> LENGTH: 21
<212> TYPE: DNA
<213> ORGANISM: Artificial Sequence
<220> FEATURE:
<223> OTHER INFORMATION: Synthetic Polypeptide

<400> SEQUENCE: 75
uucuccgaac gugucacgut t                                            21
```

TREATING HEPATITIS VIRUS INFECTION BY MODULATING MICRORNAS MIR-130A, MIR-130B, MIR-204, OR MIR-1236

RELATED APPLICATIONS

The present application is the National Stage of International Application No. PCT/US2014/056586, filed on Sep. 19, 2014, which claims priority under 35 U.S.C. §119(e) to U.S. Provisional Patent Application No. 61/880,508, filed Sep. 20, 2013, which is herein incorporated by reference in its entirety.

BACKGROUND OF THE INVENTION

MicroRNAs (miRNAs) play an important regulatory role in differentiation and development (Ambros, V. Curr Opin Genet Dev 21: 511-517 (2011)). Cellular microRNAs can affect viral replication in a positive or negative manner (Skalsky, et al. *Annu Rev Microbiol* 64: 123-141 (2010); Jopling, et al. *Science* 309:1577-1581 (2005)).

To date, it remains a challenge to completely eradicate hepatitis B virus (HBV) in chronic hepatitis B patients. Chronic infection with HBV leads to the development of hepatocellular carcinoma (HCC). Many HCC-related microRNAs have been reported (Liu, et al. *Biochimica et biophysica acta* 1809:678-685 (2011)); however, the field of HBV-related microRNA has remained to be explored and clarified. The hepatotropic HBV resides in the liver which plays an active role in glucose and lipid metabolism. Liver enriched transcription factors and coactivators have been studied for their effect on HBV enhancer/promoter, including HNF1, HNF4, C/EBPα, PPARα and PGC1α (Quasdorff, et al. 17:527-536 (2010); Bar-Yishay, et al. Liver International 31: 282-290 (2011)). Of particular interest is PGC1α, which is known to coactivate many partners (Finck, et al. The Journal of Clinical Investigation 116: 615-622 (2006)). In addition to hepatic gluconeogenesis (Yoon, et al. *Nature* 413: 131-138 (2001)), PGC1α is known to be involved in brown adipose adaptive thermogenesis (Puigserver, et al. *Cell* 92:829-839 (1998)), mitochondria biogenesis and respiration (Houten, et al. *Cell* 119:5-7 (2004)), and neurodegenerative diseases (St-Pierre, et al., *Cell* 127:397-408 (2006)). PGC1α can activate HBV transcription and replication in hepatocytes (Shlomai, et al. *Proceedings of the National Academy of Sciences of the United States of America* 103:16003-16008 (2006); and Ondracek, et al. *Journal of Virology* 83: 12535-12544 (2009)).

Recently, microRNAs have emerged as an important posttranscriptional regulator of metabolism (Rottiers, et al. *Nat Rev Mol Cell Biol* 13:239-250 (2012)). It remains to be investigated whether metabolism-related microRNAs could have an effect on hepatitis virus replication, and whether hepatitis virus infection could have an effect on liver metabolism via microRNAs.

SUMMARY OF THE INVENTION

The present disclosure is based on the unexpected discoveries that four cellular microRNAs, i.e., miR-130a, mir-130b, miR-204, and miR-1236, showed anti-HBV activities. More specifically, miR-1236 directly targets the HBV specific RNA, resulting in translational suppression; miR-130a reduces HBV RNA transcription and DNA replication; and miR-204 attenuated HBV replication by interfering with capsid assembly and pregenomic RNA (pgRNA) encapsidation.

Accordingly, one aspect of the present disclosure relates to a method for regulating replication of a hepatitis virus (e.g., a hepatitis B virus), comprising at least a step of contacting liver cells with an effective amount of (a) a miR-130a RNA, a miR-130b RNA, a miR-204 RNA, a miR-1236 RNA, or a combination thereof. The hepatitis virus can be a hepatitis B virus (HBV).

In some embodiments, the method comprises contacting liver cells with a miR-130a RNA, a miR-130b RNA, a miR-204 RNA, a miR-1236 RNA, or a combination thereof in an amount effective in inhibiting HBV replication. In some examples, the combination of all four microRNA molecules is used in this method.

In some embodiments, the miR-130a RNA, the miR-130b RNA, the miR-204 RNA, and/or the miR-1236 RNA, are duplex RNA molecule(s) or single-stranded RNA molecule.

In some examples, the miR-130a RNA, the miR-130b RNA, or both can comprise the nucleotide sequence of AGUGCAA (e.g., CAGUGCAAUGUUAAAAGGGCAU (SEQ ID NO:1)) for a miR-130a RNA and/or CAGUGCAAUGAUGAAAGGGCAU (SEQ ID NO:2) for a miR-130b RNA); the miR-204 RNA can comprise the nucleotide sequence of UUCCCUUUGUCAUCCUAUGCCU (SEQ ID NO:3); and/or the miR-1236 RNA can comprise the nucleotide sequence of CCUCUUCCCCUUGUCUCUC-CAG (SEQ ID NO:4).

In some embodiments, the contacting step is performed by administering to a subject in need thereof (e.g., a human subject such as a human patient suffering from or suspected of having HBV infection) an effective amount of the miR-130a RNA, the miR-130b RNA, the miR-204 RNA, the miR-1236 RNA, or a combination thereof, which can be naked nucleic acids or encoded by plasmids. For example, the subject can be administered with a combination of the miR-130a RNA, the miR-130b RNA, the miR-204 RNA, and the miR-1236 RNA as described herein. In some examples, the subject is administered with the miR-130a RNA, the miR-130b RNA, or a combination thereof, in an amount effective in regulating PGC1α, PGC1β, PPARγ, or a combination thereof. In other examples, the subject is administered with the miR-1236 RNA in an amount effective in reducing the level of HBV-encoded RNA. In yet other examples, the subject is administered with the miR-204 RNA in an amount effective in inhibiting HBV pregenomic RNA encapsidation, capsid assembly, or both.

Any of the microRNA molecules described herein may be co-used with another anti-HBV agent.

Also within the scope of the present disclosure are (a) pharmaceutical compositions for use in regulating replication of a hepatitis virus (e.g., inhibiting or enhancing replication of a HBV) or for treating hepatitis virus infection (e.g., HBV infection), the composition comprising a pharmaceutically acceptable carrier and one or more of a miR-130a RNA, a miR-130b RNA, a miR-204 RNA, a miR-1236 RNA as described herein; and (b) uses of any of the pharmaceutical compositions or microRNA molecules described herein for manufacturing a medicament for treating hepatitis virus infection such as HBV infection. Optionally, the pharmaceutical composition may further comprise another anti-hepatitis virus agent, such as an anti-HBV agent.

The details of one or more embodiments of the invention are set forth in the description below. Other features or advantages of the present invention will be apparent from the following drawings and detailed description of several embodiments, and also from the appended claims.

is a graph showing the efficiency of siRNA treatment for PGC1α by real time RT-qPCR. (X) is a chart showing that transfection of the stable miR-130a-expressing HepG2 cells with increasing doses of PGC1α expression vector DNA led to increased secretion of HBsAg as determined by an ELISA assay. (Y) Huh7 cells were transfected with HBV DNA and treated with PPARγ ligand, Rosiglitazone, at increasing concentrations. HBV DNA replication was increased in a dose dependent manner (upper panel). Conversely, when HBV-transfected Huh7 cells were treated with increasing dose of PPARγ antagonist, GW9662, it resulted in decreasing replication of HBV DNA (lower panel). (Z) is a chart showing that the secreted HBsAg and HBeAg were gradually reduced when HBV-transfected Huh7 cells were treated with increasing dose of PPARγ antagonist, GW9662.

Figure 4:
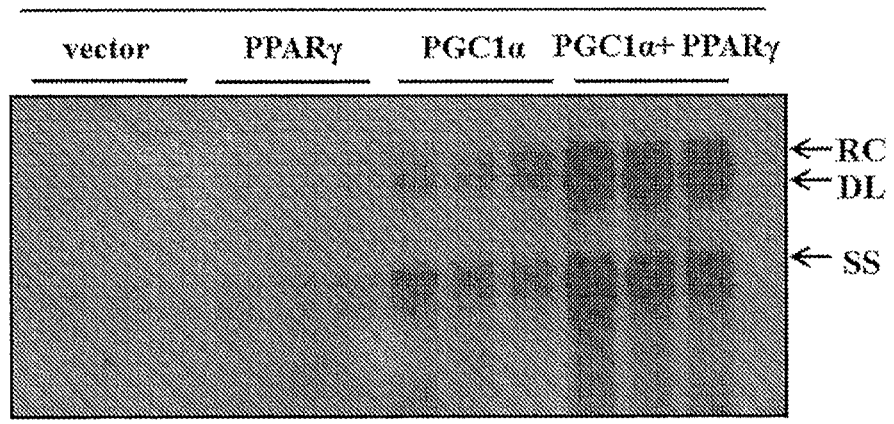
Figure 4:
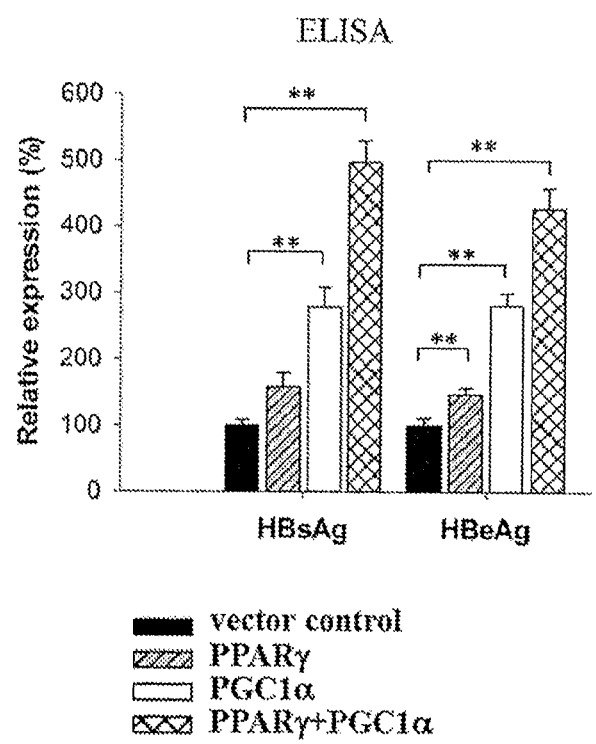
Figure 4:
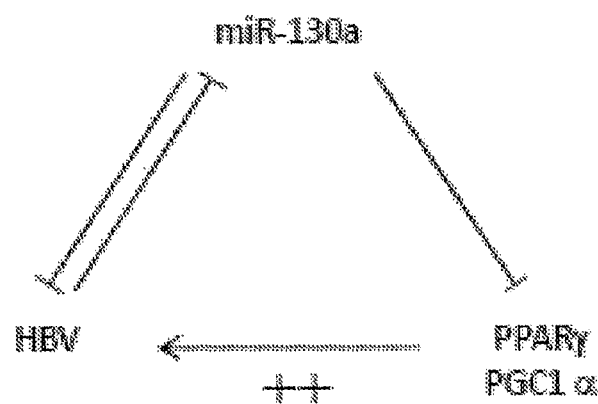
Figure 4:
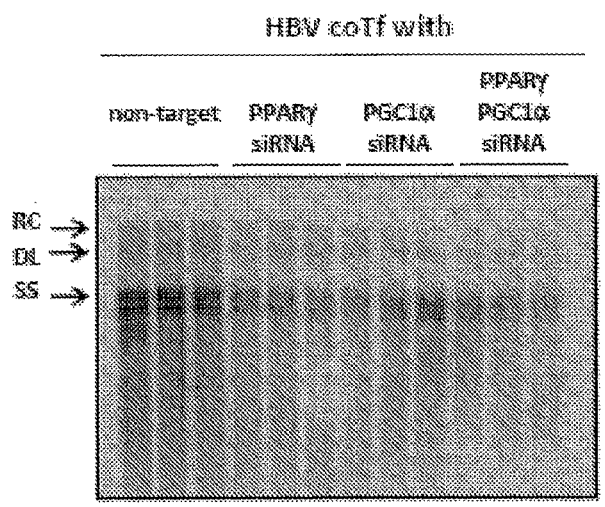
Figure 4:
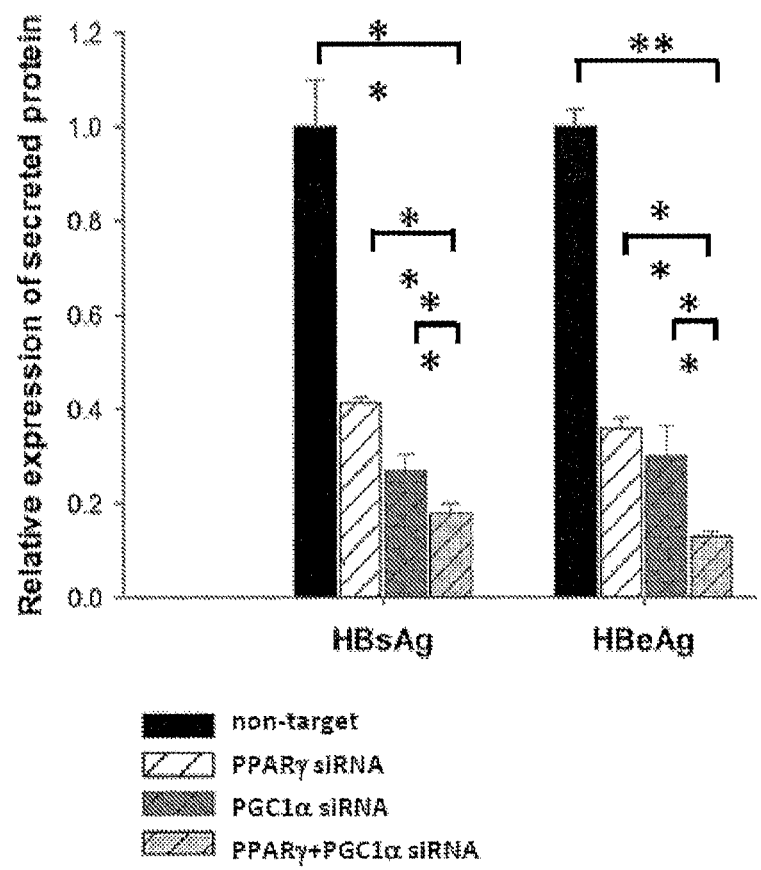

FIG. 4 shows that cotransfection of HBV DNA with both PGC1α and PPARγ expression vectors resulted in a highly potent synergistic effect on HBV DNA replication. (A) a photo showing the levels of HBV DNAs in cells co-expressing PGC1α, PPARγ, or both. (B) a chart showing the levels HBsAg and HBeAg in cells co-expressing PGC1α, PPARγ, or both. (C) a diagram summarizes the relationships among HBV, miR-130a, and host factors PGC1α and PPARγ. The symbol ++ represents a synergistic effect. (D) a photo showing cotransfection of HBV ayw dimer with the combination of both PGC1α and PPARγ siRNAs resulted in the most potent inhibitory effect on HBV DNA replication. (E) a chart showing cotransfection of HBV ayw dimer with the combination of both PGC1α and PPARγ siRNAs resulted in the most potent inhibitory effect on expression of HBsAg and HBeAg as detected by ELISA assay.

Figure 5:
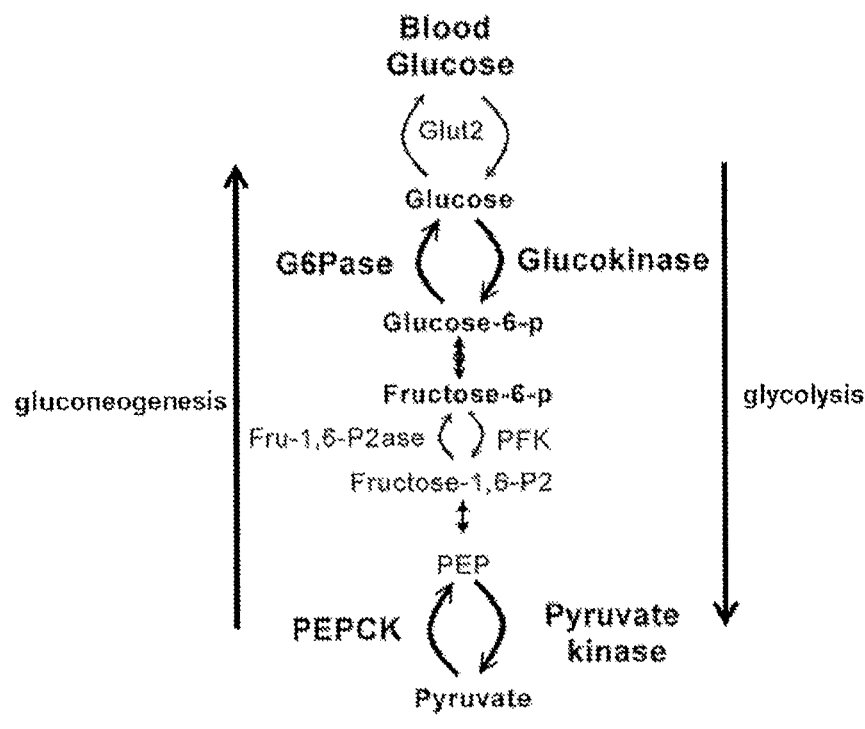
Figure 5:
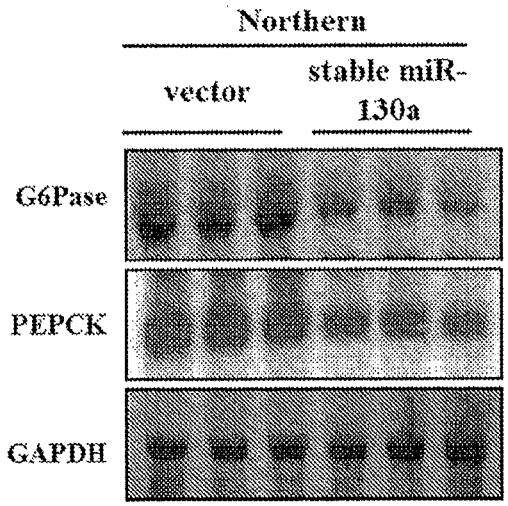
Figure 5:
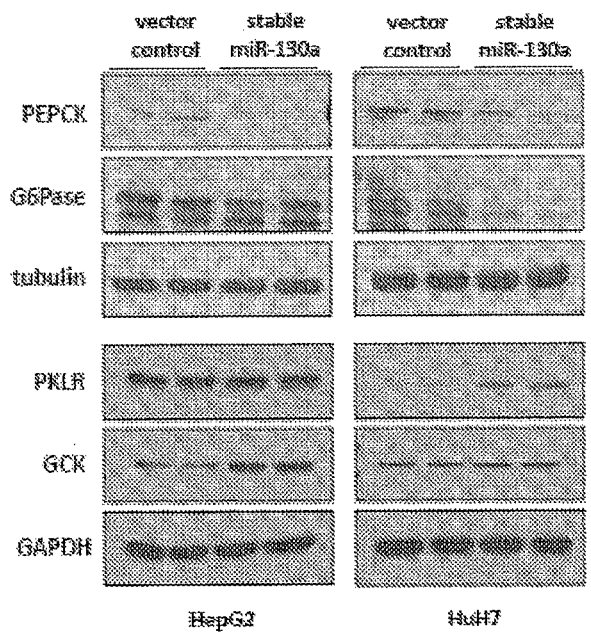
Figure 5:
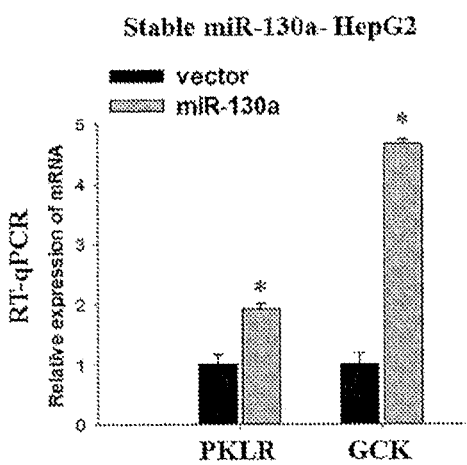
Figure 5:
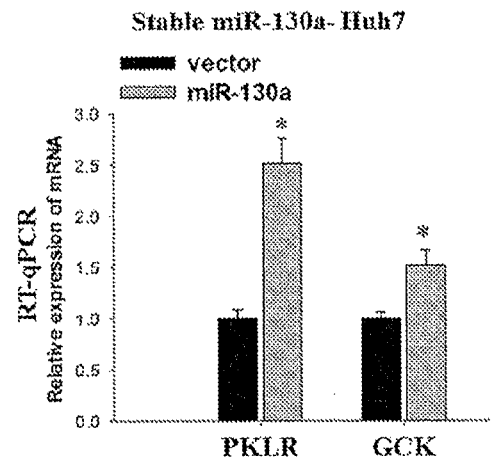
Figure 5:
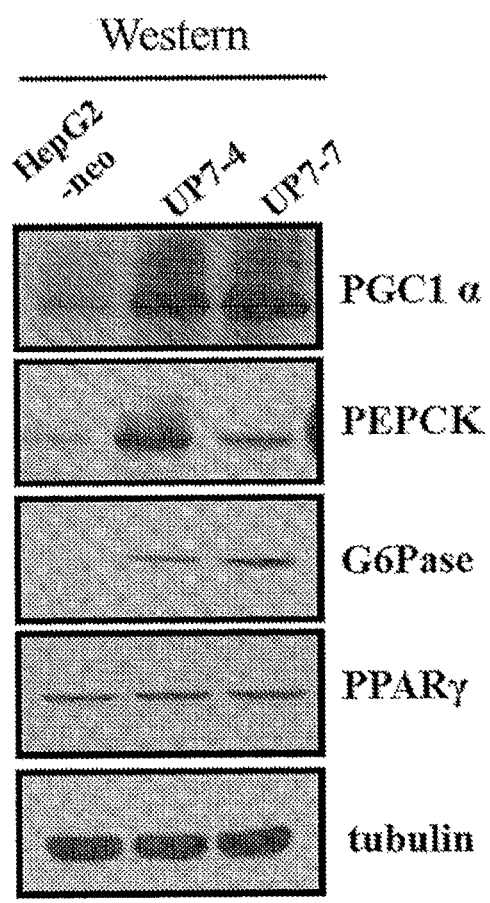
Figure 5:
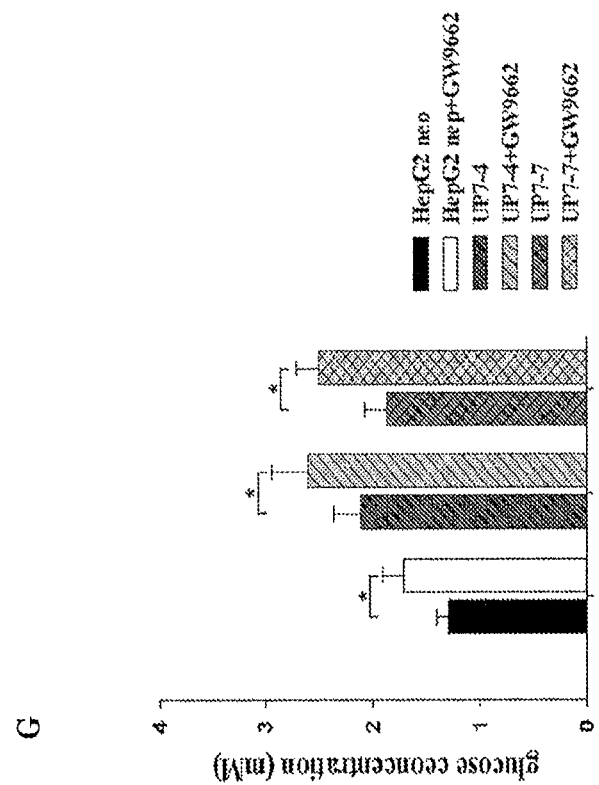
Figure 5:
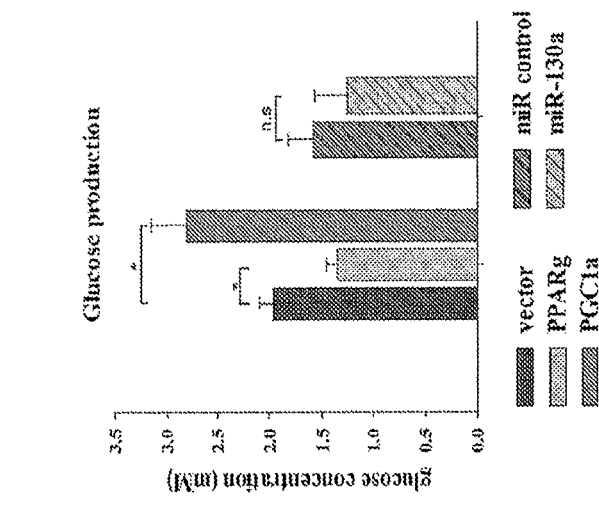
Figure 5:
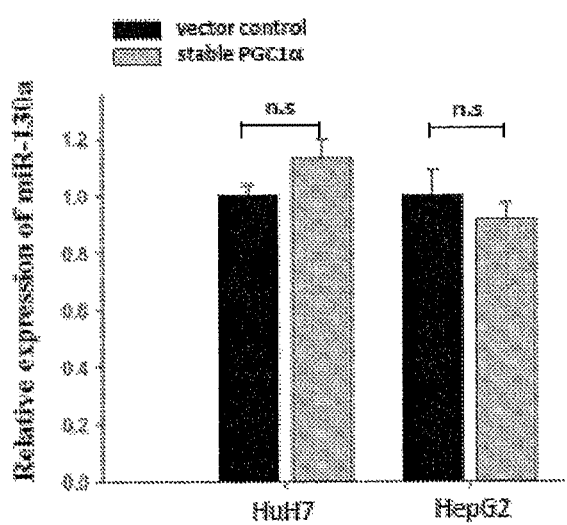
Figure 5:
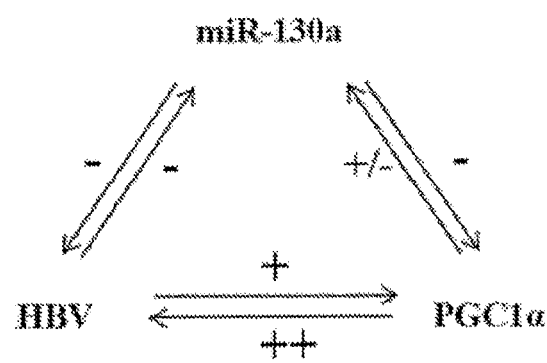
Figure 5:
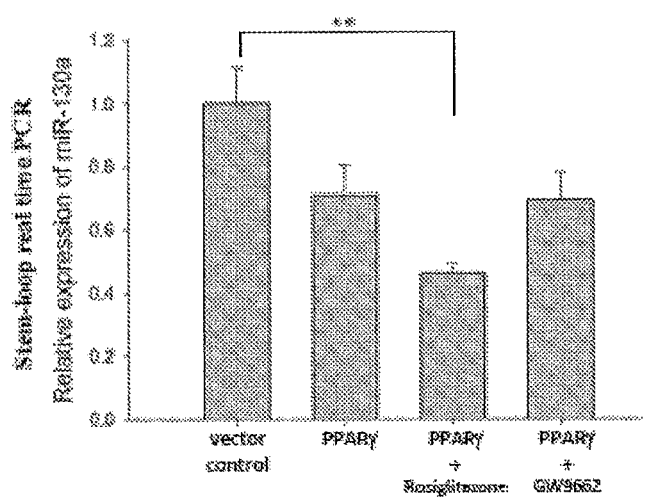
Figure 5:
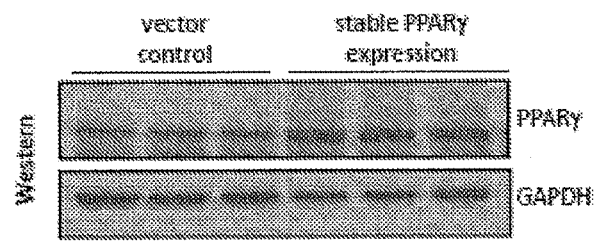
Figure 5:
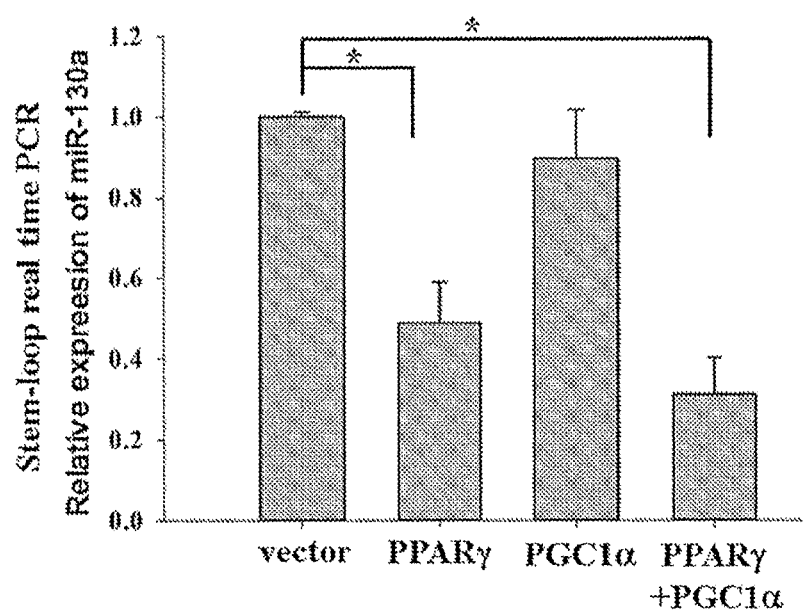
Figure 5:
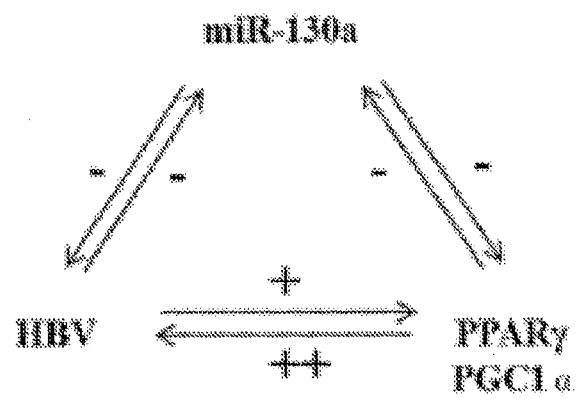
Figure 5:
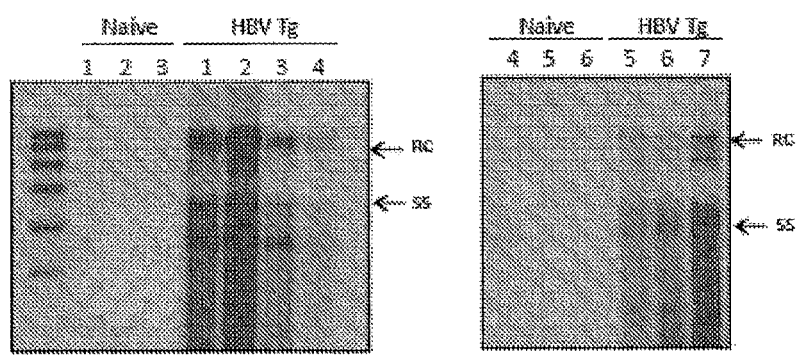
Figure 5:
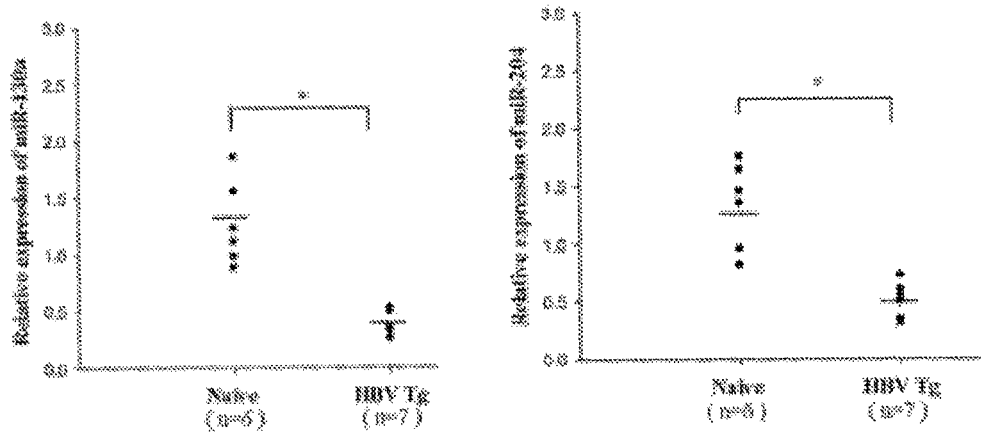
Figure 5:
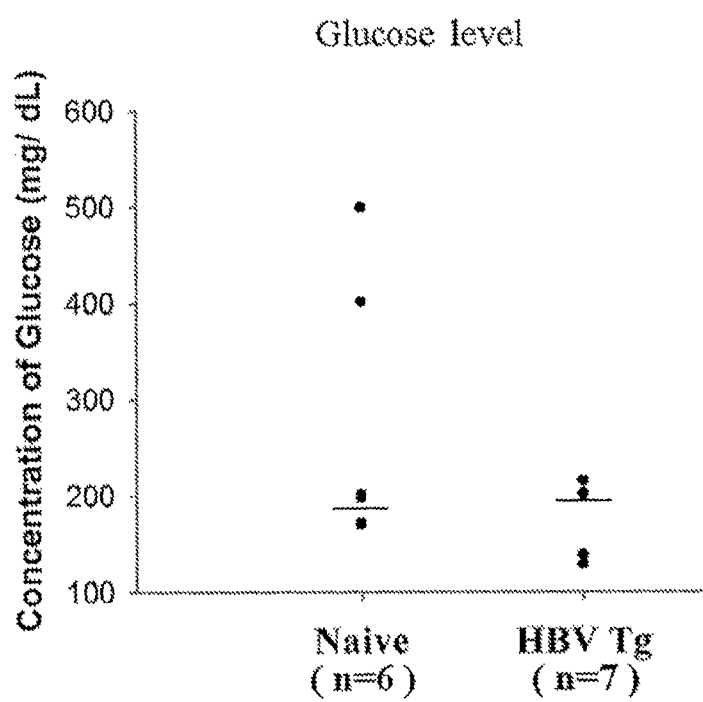
Figure 5:
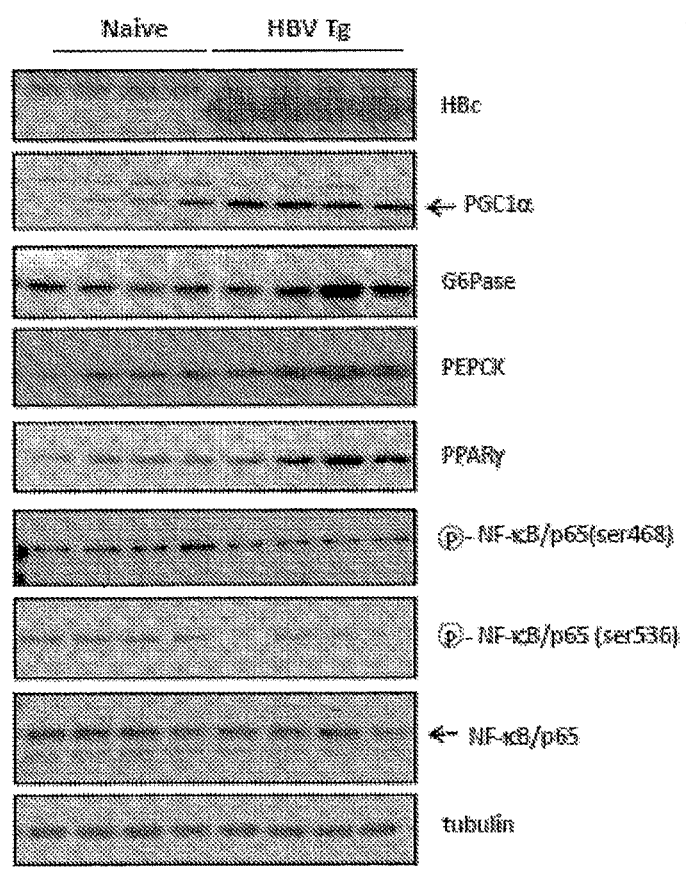

FIG. 5 is a diagram showing that miR-130a plays a regulatory role in energy metabolism in hepatocytes. (A) This diagram highlights the key enzymes in glucose metabolism. The mRNA expression of G6Pase, and PEPCK was reduced in stable miR-130a expressing HepG2 cells by Northern blot analysis. (B) Reduced protein expression of PEPCK and G6Pase was also detected by Western blot analysis. It was noted an increased level of glucokinase (GCK) in stable miR-130a expressing HepG2 cells, and an increased level of pyruvate kinase (PKLR) in stable miR-130a expressing Huh7 cells. (C) and (D) The levels of PKLR and GCK specific mRNAs were increased in stable miR-130a expressing cells by RT-qPCR analysis. (E) The protein expression of PGC1α and gluconeogenic enzymes PEPCK and G6Pase in HBV-producing HepG2 cells (UP7-4 and UP7-7) was increased by Western blot analysis. However, no significant change in PPARγ was noted. (F) Stable expression of PPARγ in HepG2 cells reduced glucose output, and conversely, expression of PGC1α stimulated glucose production. However, no significant difference in glucose levels between miR-130a expressing cells and parental cells. (G) Both stable HBV replication and a PPARγ antagonist, GW9662 (20 uM), can increase glucose production in HepG2 cells. (H) The expression of miR-130a was not affected in two stable PGC1α-expressing cell lines. (I) This diagram summarizes the relationships among PGC1α, miR-130a and HBV. +/−: neither positive nor negative effect; (J) upper panel: Reduction of miR-130a was observed in PPARγ-expressing HepG2 cell lines using stem-loop qPCR. U6 snRNA was used as an internal control. Rosiglitazone, but not GW9662, further reduced the expression of miR-130a. lower panel: Increased amounts of PPARγ protein in stable PPARγ-expressing HepG2 cell lines were detected by Western blot. (K) is a diagram showing treatment with combination of PPARγ and PGC1α exhibited a synergistic effect on miR-130a expression. (L) This triad cartoon summarizes the relationships among PPARγ, PGC1α, miR-130a and HBV. A feed-forward amplification loop among HBV and PGC1α and PPARγ can be mediated through a miR-130a intermediate. (M) HBV DNA replication was detected in the liver of HBV transgenic mice by Southern. Samples in each lane are from each individual mouse. (N) Reduced expression of miR-130a and miR-204 in HBV transgenic mice was compared to that of the parental control mice by stem-loop qPCR analysis. (O) No significant difference in glucose levels between HBV transgenic mice and the parental control mice by glucose test (Materials and Methods). (*p<0.05, n.s=no significant). (P) Relative to the wild type control mice (native), HBV transgenic mice exhibited decreased expression of NF-κB/p65 and increased expression of HBV core protein, PGC1α, PEPCK, G6Pase, PPARγ.

Figure 6:
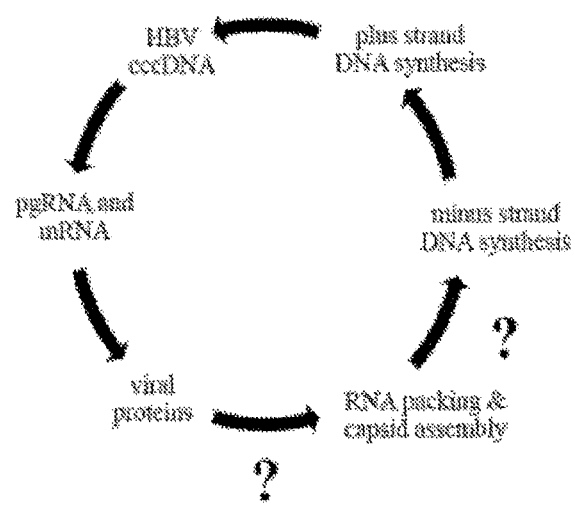
Figure 6:
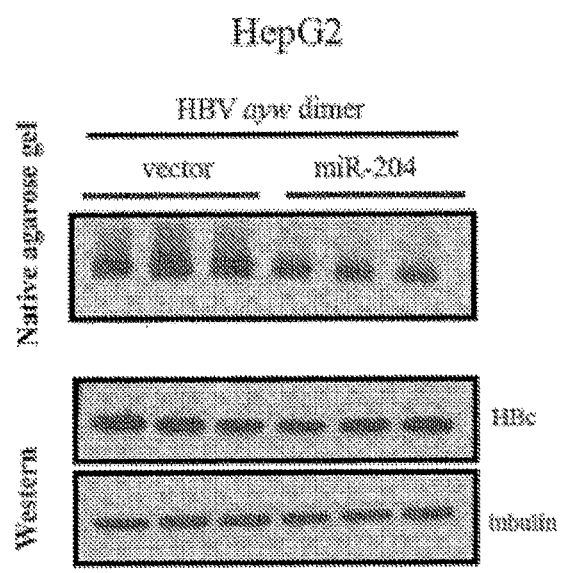
Figure 6:
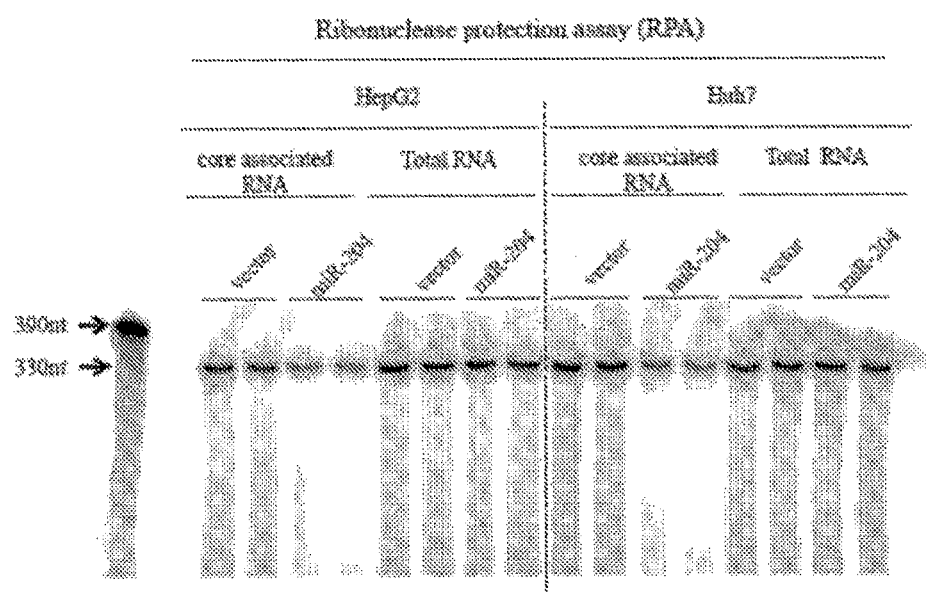

FIG. 6 is a diagram showing that miR-204 interfered with HBV RNA encapsidation and capsid assembly. (A) The summary in FIG. 2C implicated that miR-204 could interfere with either HBV capsid assembly or reverse transcription. (B) upper panel: Reduction of intracellular HBV capsid particles were detected by native agarose gel electrophoresis[26] in HepG2 cells co-transfected with HBV DNA and miR-204 expression vector. middle panel: The reduction in capsid particles was not due to the reduction of HBc protein, as assayed by denaturing SDS-PAGE and Western blot analysis. lower panel: Tubulin served as an internal control. (C) Core particle-associated RNAs of HBV polymerase mutant Y63D (Ning et al. *PLoS pathogens* 7, e1002255; 2011), with or without miR-204 cotransfection, were analyzed by ribonuclease protection assay (RPA) (Materials and Methods). Cotransfection with miR-204 reduced the levels of encapsidated HBV RNAs in HepG2 and Huh7 cells. The protected HBV RNA fragment migrated as a 330 nt species.

Figure 7:
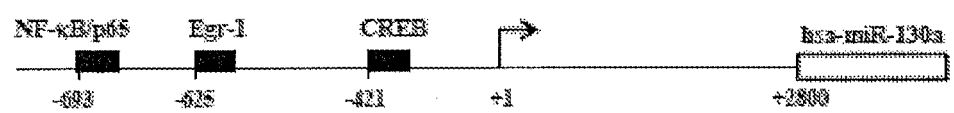
Figure 7:
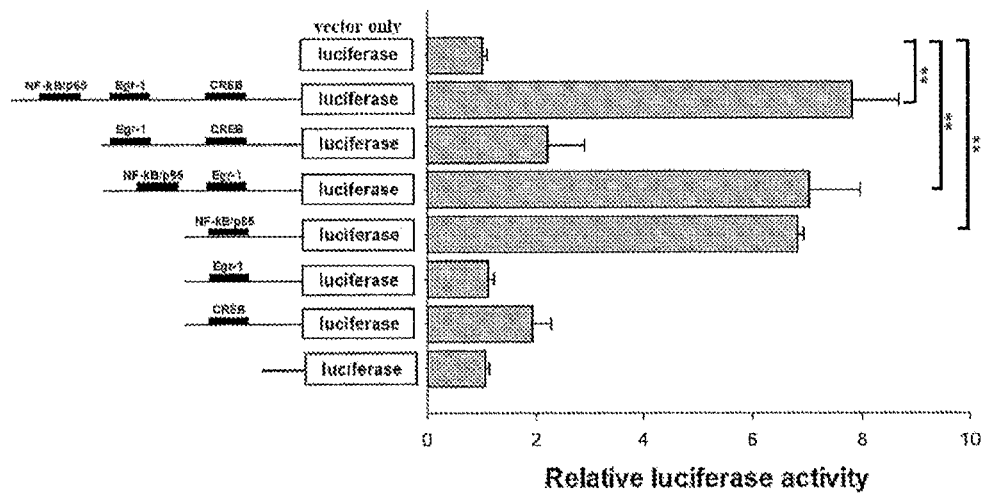
Figure 7:
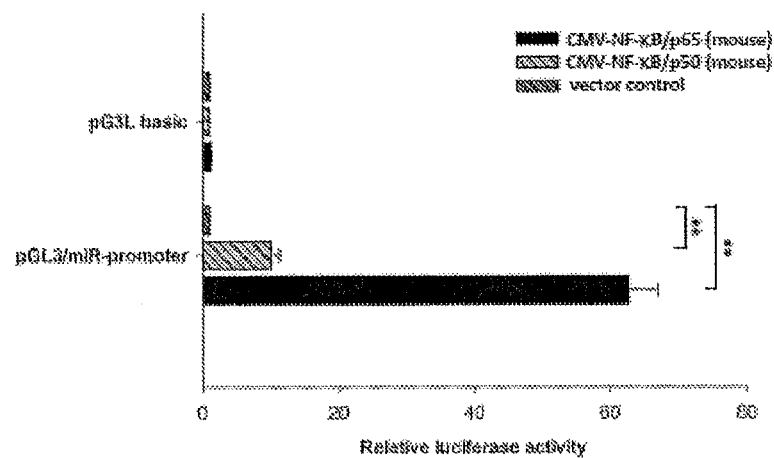
Figure 7:
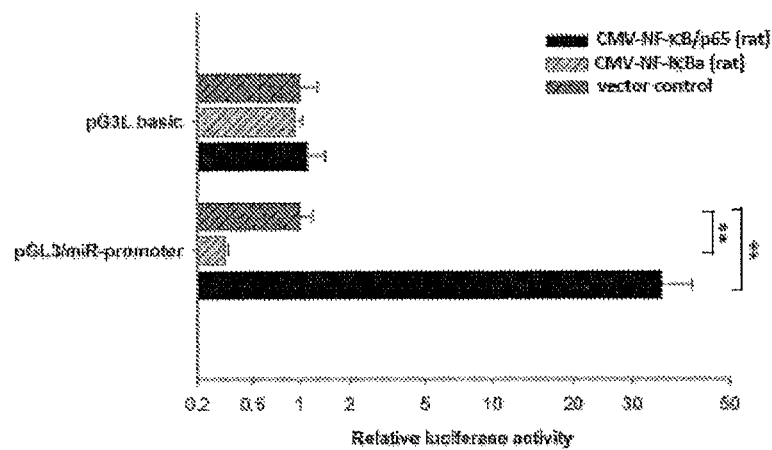
Figure 7:
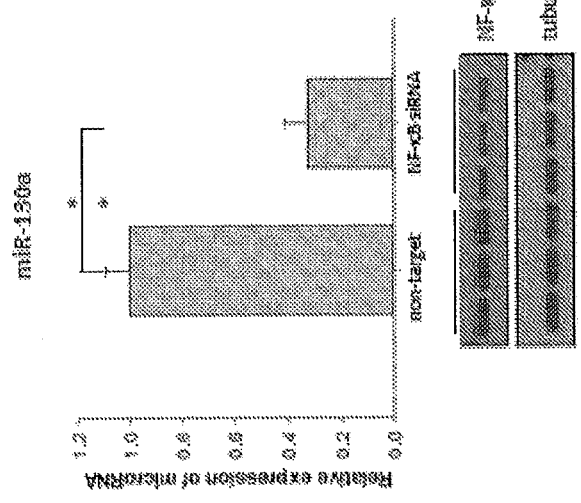
Figure 7:
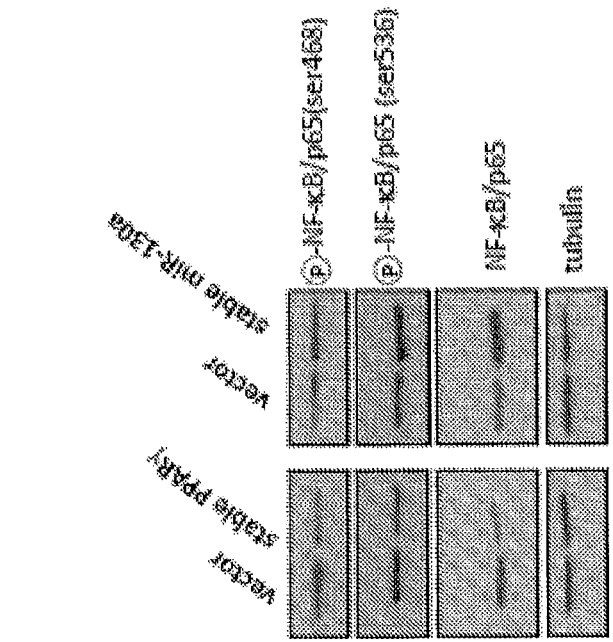
Figure 7:
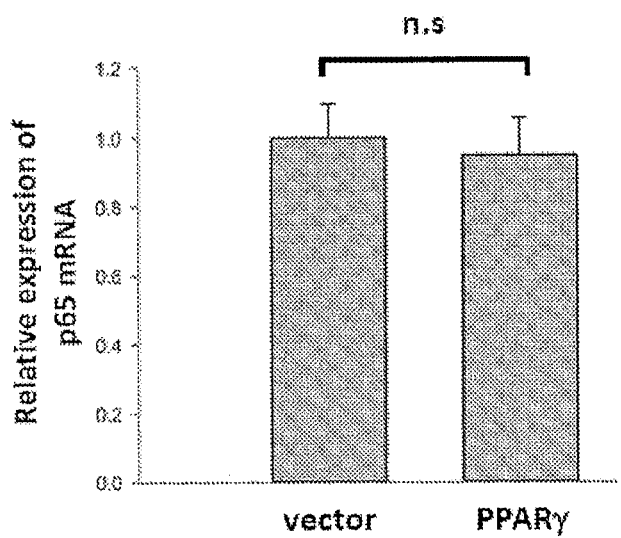
Figure 7:
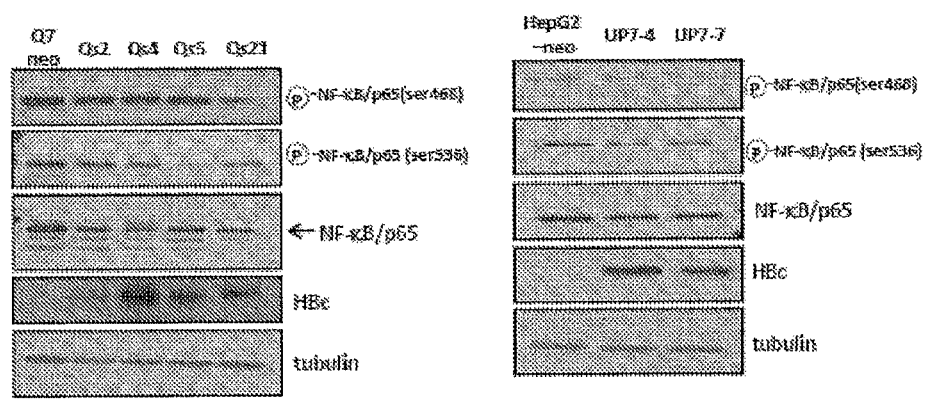
Figure 7:
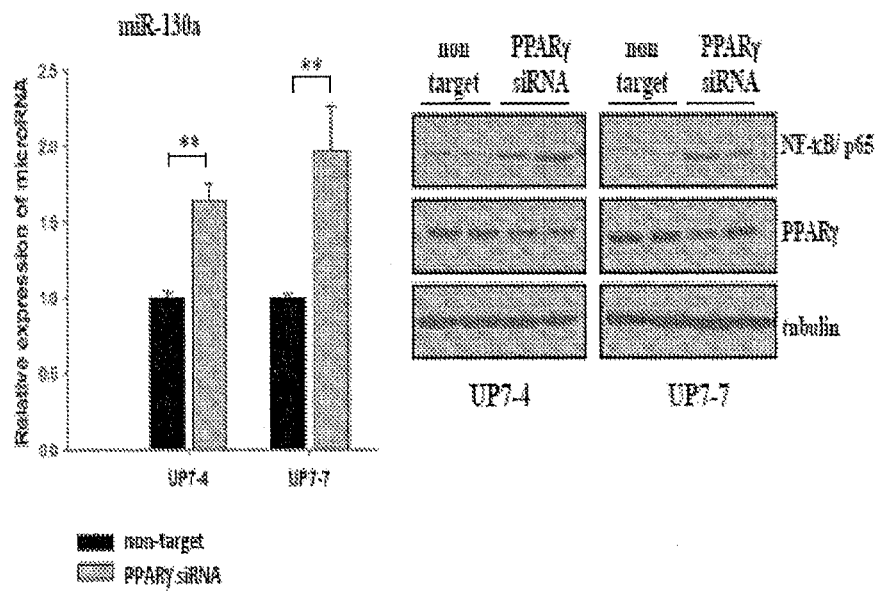
Figure 7:
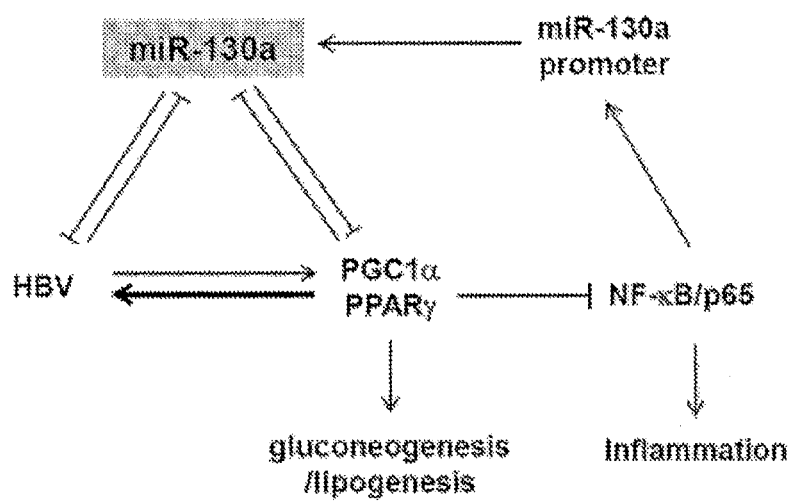

FIG. 7 shows the regulation of miR-130a expression. (A) is a schematic diagram shows several potential binding sites for transcription factors in the putative hsa-miR-130a promoter element upstream from the transcription start site (+1): a putative NF-κB/p65 binding site at −693 position was as previously reported (Zhou et al. 2010a), and the sites at −625 and −421 for Egr-1 and CREB were predicted using the online softwares Promo and TRANSFAC (Wingender et al. 2000; Messeguer et al. 2002). (B) shows the analysis of the miR-130a promoter by deletion mapping and reporter assay. HuH-7 cells were transfected with various luciferase reporter constructs containing sequentially deleted hsa-miR-130a promoter. Deletion of an NF-κB/p65 binding site resulted in significantly reduced reporter activity. (C) upper panel: Both NF-κB/p65 and p50 can stimulate miR-130a promoter activities by approximately 60-fold and 10-fold, respectively. HuH-7 cells were co-transfected with expression vectors of either pCMV-mouse NF-κB/p65 or p50, and a luciferase reporter driven by an hsa-miR-130a promoter. lower panel: A 30-fold stimulation effect on miR-130a promoter was obtained by using a rat pCMV-flag-NF-κB/p65. Co-transfection with a rat IκB expression vector repressed the luciferase activity by about 4-fold. Relative luciferase values for each transfection were normalized with co-transfected renilla expression. (D) Conversely, knockdown of the endogenous NF-κB/p65 by transfection with siRNA resulted in decreased expression of miR-130a by stem-loop PCR analysis. (E) left panel: A PPARγ stable expression cell line of HepG2 origin exhibited reduced levels of phosphorylated and total NF-κB/p65 protein by Western blot analysis. right panel: In contrast, a miR-130a stable expression cell line exhibited increased levels of phosphorylated and total NF-κB/p65 protein. (F) The relative mRNA level of NF-κB/p65 was not affected in stable PPARγ expressing HepG2 cells by qPCR. (G) The reduction of phosphorylated and total NF-κB/p65 protein was observed in stable HBV-producing rat (left panel) or human (right panel) hepatoma cells by Western blot analysis. (H) Knock-down of the endogenous PPARγ in stable HBV-producing human hepatoma cells UP7-4 and UP7-7 by siRNA treatment, resulted in increased expression of miR-130a by stem-loop PCR (left panel) and NF-κB protein production by Western blot analysis (right panel). (I) is a schematic illustration summarizing the integration of two positive feed-forward loops. The inflammation loop mediated by NF-κB/p65 could dampen the viral replication loop involving miR-130a, PGC1α, and PPARγ.

Figure 8:
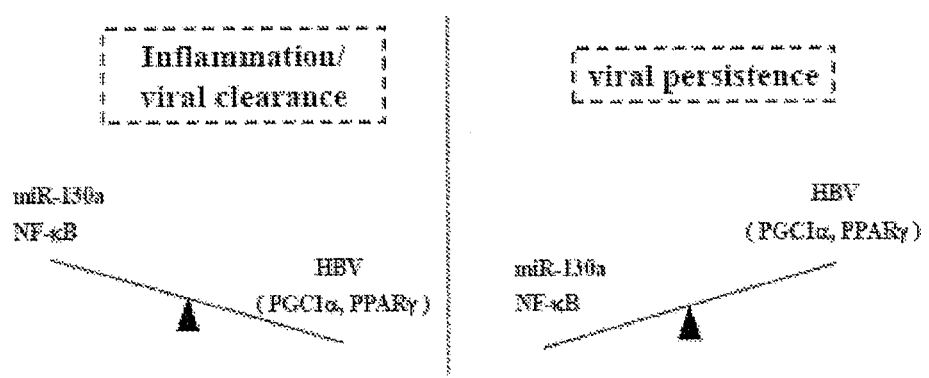

FIG. 8 is a diagram of virus-host interactions between HBV and miR-130a, NF-κB, PGC1α, and PPARγ. (A) Liver inflammation could favor viral clearance (left panel), since when NF-κB and miR-130a are elevated, PGC1α, PPARγ and HBV replication are reduced. In contrast, when liver is without inflammation (right panel), the levels of both NF-κB and miR-130a are low, and the levels of PGC1α and PPARγ are higher, resulting in more active viral replication.

Figure 9:
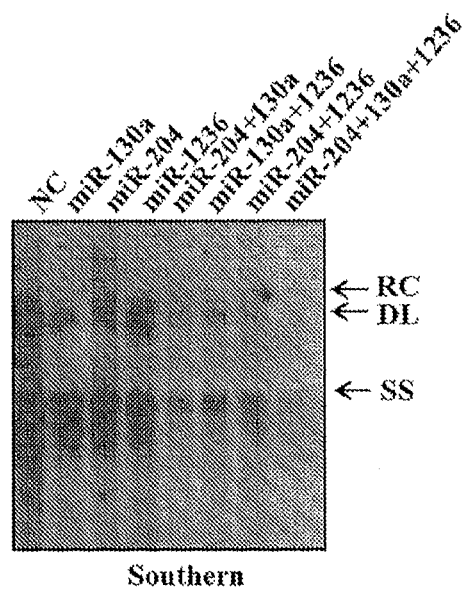
Figure 9:
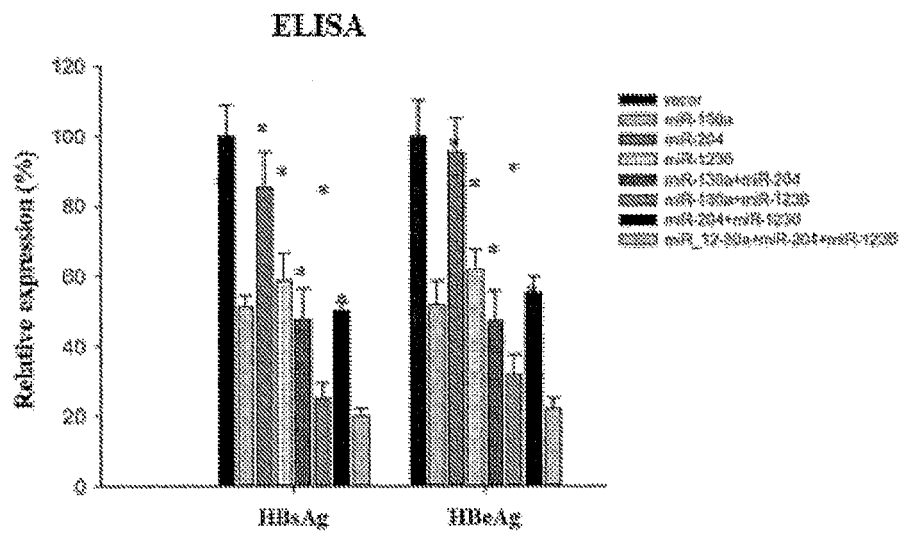

FIG. 9 includes diagrams showing that the combinations of oligonucleotides mimetics of miR-1236, miR-204, and miR-130a inhibited HBV replication and gene expression. Cotransfection of HepG2 cells with HBV DNA and oligonucleotides, mimicking miR-1236, miR-204, and miR-130a, resulted in a lower level of viral DNA replication by Southern blot analysis (A) and reduced HBsAg and HBeAg by ELISA (B). *p<0.05.

Figure 10:
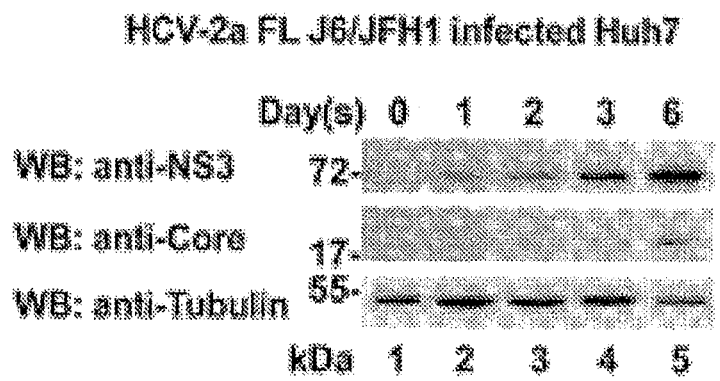
Figure 10:
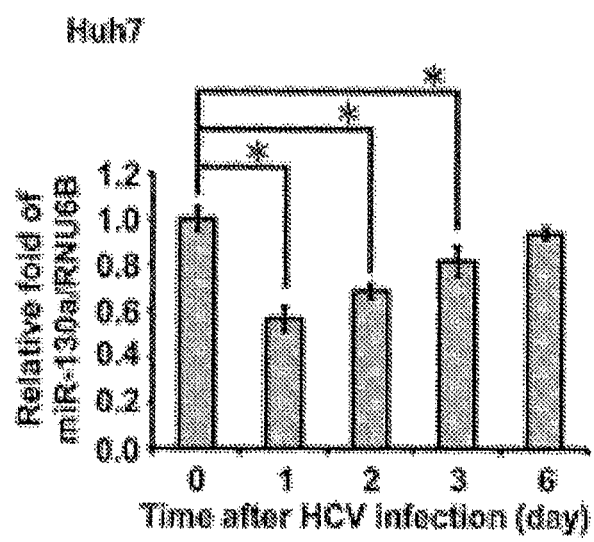
Figure 10:
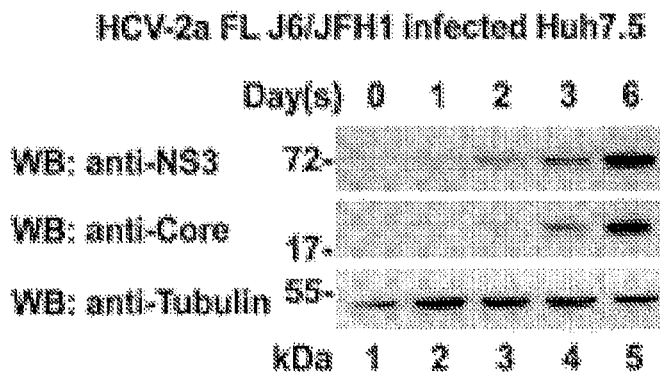
Figure 10:
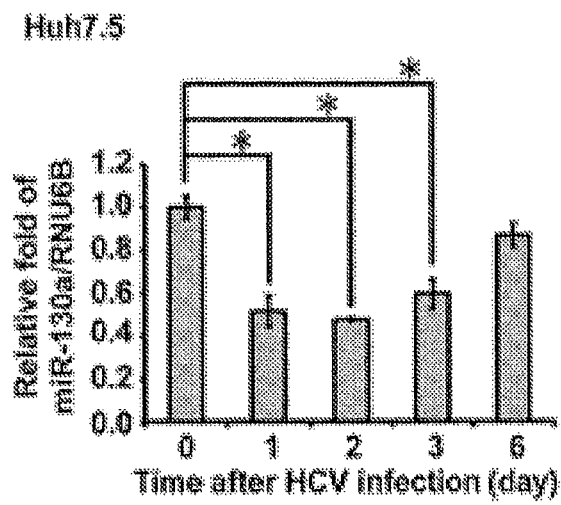

FIG. 10 is a diagram showing the time course of miR-130a expression profiles in HCV-infected Huh7 and Huh7.5 cells. (A, C) In vitro infection of Huh7 (A) and Huh7.5 (C) (MOI=1) with HCV-2a J6/JFH1 by Western blot analysis using anti-HCV NS3 and anti-HCV core antibodies. (B, D) The expression of endogenous miR-130a was measured by stem-loop qPCR in HCV infected Huh7 (B) and Huh7.5 cells (D). (P<0.05,*).

DETAILED DESCRIPTION OF THE INVENTION

The present disclosure is based on the unexpected identification of a number of cellular microRNAs, including miR-130a, miR-130b, miR-204, and miR-1236, which showed anti-HBV activities. More specifically, miR-1236 directly targets the HBV specific RNA, resulting in translational suppression; miR-130a reduces HBV RNA transcription and DNA replication; and miR-204 attenuated HBV replication by interfering with capsid assembly and pregenomic RNA (pgRNA) encapsidation. Further, miR-130a was found to be a potential regulator of HCV replication.

Thus, modulating one or more of miR-130a, miR-130b, miR-204, and miR-1236 would be effective in treating infectious diseases (e.g., infection caused by a hepatitis virus such as HBV, HCV, or HDV). Modulating a microRNA means any approach that affects the ultimate biological function of the microRNA in regulating its target gene expression. In some examples, modulating a microRNA is to regulate the cellular level of the microRNA. In other examples, modulating a microRNA is to regulate (e.g., block or enhance) its interaction with a target of the microRNA (e.g., a mRNA or a gene).

Accordingly, described herein are methods for relating replication and/or treating infection of a hepatitis virus (e.g., HBV, HCV, or HDV) using one or more of a miR-130a RNA, a miR-130b RNA (which contains the same AGUGCAA sequence as miR-130a for base pairing with a target gene), a miR-204 RNA, and a miR-1236 RNA; as well as pharmaceutical compositions for use in treating the infectious diseases described herein (e.g., HBV infection) and for use in manufacturing medicaments for those purposes.

MicroRNA Molecules

MicroRNAs are small non-coding RNA molecules (e.g., 22 nucleotides) found in many species, which regulates gene expression. miR-130a, miR-130b, miR-204, and miR-1236 are well-known microRNAs existing in many species, e.g., human. The nucleotide sequences of examples of these microRNAs (precursor and mature) are provided in MiRBase under accession numbers MI0000448 (human miR-130a), MI0000748 (human miR-130b), MI0000284 (human miR-204), and MI0006326 (human miR-1236). Exemplary nucleotide sequences of these miRNA molecules are provided below:

```
Human miR-130a:
                                    (SEQ ID NO: 11)
ugcugcuggc cagagcucuu uucacauugu gcuacugucu gcaccuguca cuagcagugc aauguuaaaa gggcauuggc cguguagug Human miR-130b:
                                    (SEQ ID NO: 12)
ggccugcccg acacucuuuc ccuguugcac uacuauaggc cgcugggaag cagugcaaug augaagggc aucggucagg uc Human miR-204:
                                    (SEQ ID NO: 13)
ggcuacaguc uuucuucaug ugacucgugg acuucccuuu gucauccuau gccugagaau auaugaagga ggcugggaag gcaaagggac guucaauugu caucacuggc Human MiR-1236:
                                    (SEQ ID NO: 14)
gugagugaca ggggaaaugg ggauggacug gaagugggca gcauggagcu gaccuucauc auggcuuggc caacauaaug ccucuucccc uugucucucc ag
```

A miR-130a RNA as described herein is an nucleic acid (e.g., an RNA molecule) that possesses the same bioactivity as a wild-type miR-130a, such as the human miR-130a, e.g., regulating the expression of PGC1α, PGC1β, and/or PPARγ. Such a RNA molecule can comprise the nucleotide sequence of miR-130a or a portion thereof (e.g., AGUGCAA or CAGUGCAAUGUUAAAAGGGCAU (SEQ ID NO:1)). A miR-130a RNA can include up to 150 (e.g., 100, 80, 60, 50, 40, 30, or less) nucleotide residues. In some examples, the miR-130a can be a duplex RNA molecule or a single-strand RNA molecule. In other examples, it can be a hairpin molecule, which may include a 21-23 sense sequence (e.g., CAGUGCAAUGUUAAAAGGGCAU (SEQ ID NO:1)), a short linker, an antisense sequence complementary to the sense sequence, and a polyT tail.

A miR-130b RNA as described herein is nucleic acid such as an RNA molecule that possesses the same bioactivity as a wild-type miR-130b, such as the human miR-130b. Since miR-130b share the same sequence as miR-130a for base pairing with target genes, miR-130b would possess the same biological functions as miR-130a, e.g., regulating the expression of PGC1α, PGC1β, and/or PPARγ. Such an RNA molecule can comprise the nucleotide sequence of miR- 130b or a portion thereof (e.g., AGUGCAA or CAGUG-CAAUGAUGAAAGGGCAU (SEQ ID NO:2)). A miR-130b RNA can include up to 150 (e.g., 100, 80, 60, 50, 40, 30, or less) nucleotide residues. In some examples, the miR-130b RNA can be a duplex RNA molecule or a single-strand RNA molecule. In other examples, it can be a hairpin molecule, which may include a 21-23 sense sequence (e.g., CAGUGCAAUGAUGAAAGGGCAU (SEQ ID NO:2)), a short linker, an antisense sequence complementary to the sense sequence, and a polyT tail.

A miR-204 RNA as described herein is a nucleic acid such as an RNA molecule that possesses the same bioactivity as a wild-type miR-204, such as the human miR-204, e.g., interfering with capsid assembly and pregenomic RNA (pgRNA) encapsidation. Such a RNA molecule can comprise the nucleotide sequence of miR-204 or a portion thereof (e.g., UUCCCUUUGUCAUCCUAUGCCU (SEQ ID NO:3)). A miR-204 RNA can include up to 150 (e.g., 100, 80, 60, 50, 40, 30, or less) nucleotide residues. In some examples, the miR-204 RNA can be a duplex RNA molecule or a single-strand RNA molecule. In other examples, it can be a hairpin molecule, which may include a 21-23 sense sequence (e.g., UUCCCUUUGUCAUCCUAUGCCU (SEQ ID NO:3)), a short linker, an antisense sequence complementary to the sense sequence, and a polyT tail.

A miR-1236 RNA as described herein is a nucleic acid such as an RNA molecule that possesses the same bioactivity as a wild-type miR-1236, such as the human miR-1236, e.g., directly targeting the HBV specific RNA, resulting in translational suppression. Such a RNA molecule can comprise the nucleotide sequence of miR-1236 or a portion thereof (e.g., CCUCUUCCCCUUGUCUCUCCAG (SEQ ID NO:4)). A miR-1236 RNA can include up to 150 (e.g., 100, 80, 60, 50, 40, 30, or less) nucleotide residues. In some examples, the miR-1236 RNA can be a duplex RNA molecule or a single-strand RNA molecule. In other examples, it can be a hairpin molecule, which may include a 21-23 sense sequence (e.g., CCUCUUCCCCUUGUCUCUCCAG (SEQ ID NO:4)), a short linker, an antisense sequence complementary to the sense sequence, and a polyT tail.

When necessary, the microRNA molecules can include non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the oligonucleotide/RNA molecules described herein has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the microRNA molecules described herein includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the microRNA molecules described herein includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the microRNA molecules to their targeting sites. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the microRNAs described herein can be prepared by conventional methods, e.g., chemical synthesis or in vitro transcription. Their intended bioactivity as described herein can be verified by routine methods, e.g., those described in the Examples below.

Medical Treatments

The miR-130a, miR-130b, miR-204, and miR-1236 RNAs, either alone or in combination, can be used in regulating (e.g., inhibiting) hepatitis virus replication (e.g., in vivo or in vitro) or in treating hepatitis virus infection, including replication/infection of HBV, HCV, or HDV.

The term "treating" as used herein refers to the application or administration of a composition including one or more active agents to a subject, who has hepatitis virus infection (e.g., HBV) infection, suspected of having such an infection, or is at risk for the infection with the purpose to cure, heal, alleviate, relieve, alter, remedy, ameliorate, improve, or affect the infection, the symptoms of the infection, or the predisposition toward the infection.

To perform the treatment described herein, one or more microRNA molecules as described herein can be administered to a subject in need of the treatment via a suitable route. The one or more microRNA molecules can be administered to a subject in need of the treatment directly or indirectly (e.g., via one or more expression vectors adapted for expressing the microRNA molecules, or via naked RNA molecules). Such an expression vector can be constructed by inserting one or more nucleotide sequences of the microRNA(s) into a suitable expression vector, in which the microRNA sequences are in operable linkage with a suitable promoter.

One or more of the miR-130a RNA, miR-130b RNA, miR-204 RNA, and miR-1236 RNA, or one or more expression vectors suitable for expressing such can be mixed with a pharmaceutically acceptable carrier to form a pharmaceutical composition. An "acceptable carrier" is a carrier compatible with the active ingredient of the composition (and preferably, stabilizes the active ingredient) and not deleterious to the subject to be treated. Suitable carriers include, but are not limited to, (a) salts formed with cations (e.g., sodium, potassium, ammonium, magnesium, calcium) and polyamines (e.g., spermine and spermidine); (b) acid addition salts formed with inorganic acids (e.g., hydrochloric acid, hydrobromic acid, sulfuric acid, phosphoric acid, nitric acid); (c) salts formed with organic acids (e.g., acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid); and (d) salts formed from elemental anions (e.g., chlorine, bromine, and iodine). Other suitable carriers include microcrystalline cellulose, mannitol, glucose, defatted milk powder, polyvinylpyrrolidone, starch, and a combination thereof. See, e.g., Remington's Pharmaceutical Sciences, Edition 18, Mack Publishing Co., Easton, Pa. (1995); and Goodman and Gilman's "The Pharmacological Basis of Therapeutics", Tenth Edition, Gilman, J. Hardman and L. Limbird, eds., McGraw-Hill Press, 155-173, 2001.

To facilitate delivery, the microRNA molecules, or the expression vectors thereof can be conjugated with a chaperon agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperon agent is a micelle, liposome, nanoparticle, or microsphere, in which the microRNA molecules or expression vectors are encapsulated. Methods for preparing such a micelle, liposome, nanoparticle, or microsphere are well known in the art. See, e.g., U.S. Pat. Nos. 5,108,921; 5,354,844; 5,416,016; and 5,527,5285.

In another example, the chaperon agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the microRNA described herein into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellittin). Other examples include polyhistidine, polyimidazole, polypyridine, polypropyleneimine, and a polyacetal substance (e.g., a cationic polyacetal).

A condensing agent interacts with the microRNA or the expression vector, causing it to condense (e.g., reduce the size of the oligonucleotide), thus protecting it against degradation. Preferably, the condensing agent includes a moiety (e.g., a charged moiety) that interacts with the oligonucleotide via, e.g., ionic interactions. Examples of condensing agents include polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and alpha helical peptide.

In some embodiments, an effective amount of a miR-130a RNA, a miR-130b RNA, a miR-204 RNA, a miR-1236 RNA, or a combination thereof is administered to a subject (e.g., a human patient) suffering from, suspected of having, or at risk for hepatitis virus infection (e.g., HBV infection) via a suitable route. In other embodiments, an effective amount of one or more expression vectors for producing the one or more microRNA molecules are administered to such a subject. When miR-130a, miR-130b, or both are used, the amount of this molecule or its expression vector can be effective in regulating PGC1α, PGC1β, PPARγ, or all three. When miR-204 is used, the amount of this molecule or its expression vector can be effective in regulating (e.g., inhibiting) HBV pregenomic RNA encapsidation, capsid assembly, or both. When miR-1236 is used, the amount of this molecule or its expression vector can be effective in reducing the level of HBV-encoded RNA.

Any of the microRNA molecules or a combination thereof can be used in an in vitro assay to regulate (e.g., inhibit) the replication of HBV virus, e.g., by contacting an effective amount of one or more the microRNA molecules, or one or expression vectors thereof with liver cells infected with an hepatitis virus (e.g., HBV).

"An effective amount" as used herein refers to the amount of a microRNA molecule or an expression vector thereof, that alone, or together with further doses or one or more other active agents, produces the desired response, e.g., inhibiting HBV replication, interfering with HBV pregenomic RNA encapsidation and/or capsid assembly, and/or reducing the level of HBV-encoded RNA. In the case of treating HBV infection, the desired response may be inhibiting the progression of the disease. This may involve only slowing the progression of the disease temporarily, although more preferably, it involves halting the progression of the disease permanently. This can be monitored by routine methods, such as physical examination and suitable lab tests. The desired response to treatment of HBV infection also can be delaying the onset or even preventing the onset of the disease.

Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The interrelationship of dosages between animals and humans (e.g., based on milligrams per meter squared of body surface or milligrams per body weight) is well known in the art. See, e.g., Freireich et al., (1966) *Cancer Chemother Rep* 50: 219. Body surface area may be approximately determined from height and weight of the patient.

A subject in need of any of the above-described treatments can be a subject (e.g., a human) suffering from, suspected of having, or at risk for developing the hepatitis virus infection (e.g., HBV infection). Such a subject can be identified via a routine medical procedure, including, but are not limited to, physical examination and pathological analysis. A subject suspected of having the infection may show one or more symptoms of the infection. For example, common symptoms of HBV infection include, but are not limited to, fever, fatigue, muscle or joint pain, loss of appetite, mild nausea and/or vomiting. A subject at risk for developing hepatitis virus infection (e.g., HBV infection) possesses one or more risk factors associated with the infection.

Conventional methods, known to those of ordinary skill in the art of medicine, can be used to administer to a subject in need of the treatment the pharmaceutical composition described above. For example, the pharmaceutical composition described above can be delivered orally or parenterally. Parenteral administration includes intravenous, intraarterial, subcutaneous, intraperitoneal or intramuscular injection or infusion; or intracranial administration (e.g., intrathecal or intraventricular).

An injectable composition containing an microRNA molecule described herein or an expression vector thereof may contain various carriers such as vegetable oils, dimethylactamide, dimethylormamide, ethyl lactate, ethyl carbonate, isopropyl myristate, ethanol, and polyols (glycerol, propylene glycol, liquid polyethylene glycol, and the like). For intravenous injection, the oligonucleotide can be administered by the drip method, whereby a pharmaceutical formulation containing the oligonucleotide and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of a peptide, can be dissolved and administered in a pharmaceutical excipient such as sterile water, 0.9% saline, or 5% glucose solution.

When oral administration is applied, it is preferred that the oligonucleotide includes at least one 2'-O-methoxyethyl modification. A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. The pharmaceutical composition described herein can also be administered in the form of suppositories for rectal administration.

Any of the microRNA molecules may be co-used with another anti-infectious agent, such as an anti-HBV agent. Anti-HBV agents include, but are not limited to, interferons, (interferon alfa-2b and pegylated interferon alfa-2a), and nucleoside reverse transcriptase inhibitors (NRTIs) such as adefovir, entecavir, lamivudine, telbivudine, and tenofovir.

The term "co-administration" is meant to refer to a combination therapy by any administration route in which two or more agents are administered to a patient or subject. Co-administration of agents may also be referred to as combination therapy or combination treatment. The agents may be in the same dosage formulations or separate formulations. For combination treatment with more than one active agent, where the active agents are in separate dosage formulations, the active agents can be administered concurrently, or they each can be administered at separately staggered times. The agents may be administered simultaneously or sequentially (e.g., one agent may directly follow administration of the other or the agents may be give episodically, e.g., one can be given at one time followed by the other at a later time, e.g., within a week), as long as they are given in a manner sufficient to allow both agents to achieve effective concentrations in the body. The agents may also be administered by different routes, e.g., one agent may be administered intravenously while a second agent is administered intramuscularly or orally. Thus, the anticancer agent may be administered prior to, concomitant with, or after the administration of the peripheral opioid antagonists. Co-administrable agents also may be formulated as an admixture, as, for example, in a single formulation or single tablet. These formulations may be parenteral or oral, such as the formulations described, e.g., in U.S. Pat. Nos. 6,277,384; 6,261,599; 5,958,452 and PCT publication No. WO 98/25613, each hereby incorporated by reference.

Kits

The present disclosure also provides kits for use in regulating (e.g., inhibiting) hepatptis virus replication (e.g., HBV, HCV, or HDV replication) and treating hepatitis virus infection such as HBV infection. Such kits can include one or more containers comprising one or more of the microRNA molecules, or expression vectors thereof.

In some embodiments, the kit can comprise instructions for use in accordance with any of the methods described herein. The included instructions can comprise a description of administration of the microRNA(s), or the expression vector(s) thereof to treat a desired target disease. The kit may further comprise a description of selecting an individual suitable for treatment based on identifying whether that individual has the target infection.

The instructions relating to the use of an microRNA as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicating that the composition is used for inhibiting HBV, HCV, or HDV replication may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a microRNA molecule or its expression vector as described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Treating Hepatitis Virus Infection by Modulating MicroRNAs miR-130a, miR-130b, miR-204, or miR-1236

Materials and Methods
Construction of miRNA Plasmids

The sequences of human miRNAs were retrieved from Ensembl database and miRbase (Version 16) as noted above. The primer sequences used in cloning the full length precursor miRNAs are listed in Table 1 below:

TABLE 1

DNA sequences of synthetic oligonucleotides and PCR primers used in this study

| Primer name | sequences | SEQ ID NO: |
|---|---|---|
| hsa-miR-31-F | 5'-CATCTTCAAAAGCGGACACTC-3' | 15 |
| hsa-miR-31-R | 5'-TCATGGAAATCCACATCCAA-3' | 16 |
| hsa-miR-130a-F | 5'-GGCAAAAGGAAGAGTGGTGA-3' | 17 |
| hsa-miR-130a-R | 5'-ACCAGGGTAGCTGACTGGTG-3' | 18 |
| HBV ayw nt 1521-2122 F | 5'-AGCAGGTCTGGAGCAAACAT-3' | 19 |
| HBV ayw nt 1521-2122 R | 5'-CACCCACCCAGGTAGCTAGA-3' | 20 |
| HBV ayw nt 1521-2122 mt F | 5'-GGAGGAGTTGGGAGAGGAAATTAGGTTAAAGG-3' | 21 |
| HBV ayw nt 1521-2122 mt R | 5'- CCTTTAACCTAATTTCCTCTCCCAACTCCTCC-3' | 22 |
| hsa-PGC1a 3'UTR-F | 5'- ATATTCTAGAGCTTGTTCAGCGGTTCTTTC-3' | 23 |
| hsa-PGc1a 3'UTR-R | 5'- ATAT TCTAGA AGCCATCAAGAAAGGACACA-3' | 24 |
| hsa-PGC1a 3'UTR mt-F | 5'- GCAGTGTTTCTACTTGCTCAAGCATGGCCTCT-3' | 25 |
| hsa-PGc1a 3'UTR mt-R | 5'- AGAGGCCATGCTTGAGCAAGTAGAAACACTGC-3' | 26 |
| hsa-miR-130a mt-F | 5'- GCACCTGTCACTAGCTGAGCAATGTTAAAAGG-3' | 27 |
| hsa-miR-130a mt-R | 5'- CCTTTTAACATTGCTCAGCTAGTGACAGGTGC-3' | 28 |
| miR-130a sponge-F | 5'- GCACTGCTCGAGATGCCCTTTTAACATTGCACTGGAATTCATGCCCTTTTAACATTGCACTGCTCGAGATGCC-3' | 29 |
| miR-130a sponge-R | 5'- GCATCTCGAGCAGTGCAATGTTAAAAGGGCATGAATTCCAGTGCAATGTTAAAAGGGCATCTCGAGCAGTGC-3' | 30 |
| hsa-SP1 3'UTR-F | 5'- ATATCTCGAGAGATGCATTCACAGGGGTTg-3' | 31 |

TABLE 1-continued

DNA sequences of synthetic oligonucleotides and PCR primers used in this study

| Primer name | sequences | SEQ ID NO: |
|---|---|---|
| hsa-SP1 3'UTR-R | 5'-ATATCTCGAGGCTCAGAGCAGCTAATGAAG-3' | 32 |
| hsa-PPARg 3'UTR-F | 5'-ATATCTCGAGCAGAGAGTCCTGAGCCACT-3' | 33 |
| hsa-PPARg 3'UTR-R | 5'-ATATCTCGAGGGGTGGGAAACACACAAGA-3' | 34 |
| Q-PCR hsa-SOD2-F | 5'-CCACTGCTGGGGATTGATGT-3' | 35 |
| Q-PCR hsa-SOD2-R | 5'-GAGCTTAACATACTCAGCATAACG-3' | 36 |
| Q-PCR hsa-GPx1-F | 5'-GCGGGGCAAGGTACTACTTAT-3' | 37 |
| Q-PCR hsa-GPx1-R | 5'-CGTTCTTGGCGTTCTCCTGA-3' | 38 |
| Q-PCR hsa-CYCS-F | 5'-GGAGCGAGTTTGGTTGCACT-3' | 39 |
| Q-PCR hsa-CYCS-R | 5'-GTGGCACTGGGAACACTTCA-3' | 40 |
| Q-PCR hsa-Acly-F | 5'-CCTGCCATGCCACAAGATTC-3' | 41 |
| Q-PCR hsa-Acly-R | 5'-TCTGCATGCCCCACACAAT-3' | 42 |
| Q-PCR hsa-ApoE-F | 5'-CCTTCCCCAGGAGCCGAC-3' | 43 |
| Q-PCR hsa-ApoE-R | 5'-GCTCTGTCTCCACCGCTT-3' | 44 |
| Q-PCR hsa-GCK-F | 5'-TACATGGAGGAGATGCAGAATg-3' | 45 |
| Q-PCR hsa-GCK-R | 5'-ACTTGCCACCTATGAGCTTCTC-3' | 46 |
| Q-PCR hsa-PKLR-F | 5'-GAGATCCCAGCAGAGAAGGTTT-3' | 47 |
| Q-PCR hsa-PKLR-R | 5'-AGTCTCCCCTGACAGCATGA-3' | 48 |
| Q-PCR hsa-PPARg-F | 5'-CATAAAGTCCTTCCCGCTGA-3' | 49 |
| Q-PCR hsa-PPARg-R | 5'-TCTGTGATCTCCTGCACAGC-3' | 50 |
| Q-PCR hsa-HNF1-F | 5'-ACCTCATCATGGCCTCACTT-3' | 51 |
| Q-PCR hsa-HNF1-R | 5'-GTTGATGACCGGCACACTC-3' | 52 |
| Q-PCR hsa-HNF4-F | 5'-GAGCTGCAGATCGATGACAA-3' | 53 |
| Q-PCR hsa-HNF4-R | 5'-TACTGGCGGTCGTTGATGTA-3' | 54 |
| Q-PCR hsa-PPARa-F | 5'-CCTCTCAGGAAAGGCCAGTA-3' | 55 |
| Q-PCR hsa-PPARa-R | 5'-CACTTGATCGTTCAGGTCCA-3' | 56 |
| Q-PCR hsa-ESRRg-F | 5'-GGAGAACAGCCCATACCTGA-3' | 57 |
| Q-PCR hsa-ESRRg-R | 5'-GCCCATCCAATGATAACCAC-3' | 58 |
| Q-PCR hsa-CEBPb-F | 5'-GACAAGCACAGCGACGAGTA-3' | 59 |
| Q-PCR hsa-CEBPb-R | 5'-AGCTGCTCCACCTTCTTCTG-3' | 60 |
| Q-PCR hsa-CEBPa-F | 5'-CAGACCACCATGCACCTG-3' | 61 |
| Q-PCR hsa-CEBPa-R | 5'-CTCGTTGCTGTTCTTGTCCA-3' | 62 |
| Q-PCR hsa-SP1-F | 5'-GCACCTGCCCCTACTGTAAA-3' | 63 |
| Q-PCR hsa-SP1-R | 5'-GCGTTTCCCACAGTATGACC-3' | 64 |
| Q-PCR hsa-ESRRa-F | 5'-TGGCTACCCTCTGTGACCTC-3' | 65 |
| Q-PCR hsa-ESRRa-R | 5'-CCCCTCTTCATCCAGGACTA-3' | 66 |
| Q-PCR hsa-LRH-F | 5'-ATCCTCGACCACATTTACCG-3' | 67 |
| Q-PCR hsa-LRH-R | 5'-TGCCACTAACTCCTGTGCAT-3' | 68 |

TABLE 1-continued

DNA sequences of synthetic oligonucleotides and PCR primers used in this study

| Primer name | sequences | SEQ ID NO: |
|---|---|---|
| Q-PCR hsa-PGC1a-F | 5'- TATCAGCACGAGAGGCTGAA-3' | 69 |
| Q-PCR hsa-PGC1a-R | 5'- TCAAAACGGTCCCTCAGTTC-3' | 70 |
| Q-PCR hsa-Scd1-F | 5'- GCAAACACCCAGCTGTCAAA-3' | 71 |
| Q-PCR hsa-Scd1-R | 5'- GCACATCATCAGCAAGCCAG -3' | 72 |
| Q-PCR hsa-Acsl1-F | 5'-GAGTGGGCTGCAGTGACA -3' | 73 |
| Q-PCR hsa-Acsl1-R | 5'-GCACGTACTGTCGGAAGTCA -3' | 74 |

Figure 1:
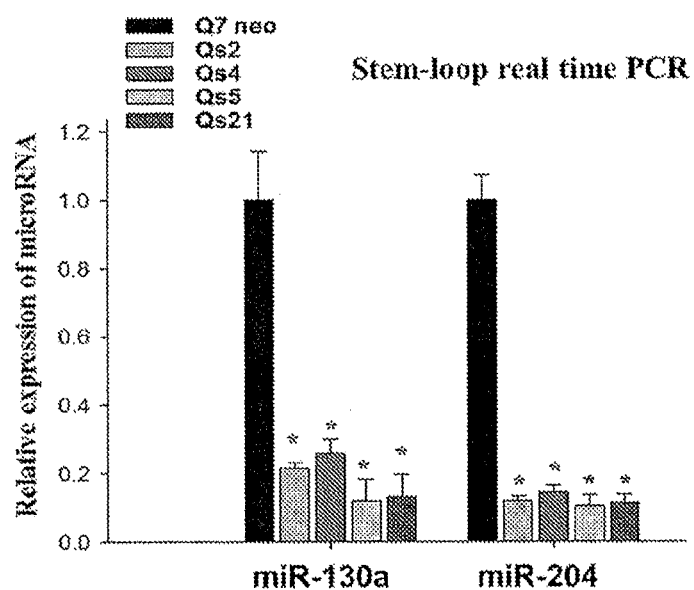
FIG. 1 is a diagram showing that human miR-130a, miR-204, and miR-1236 each attenuated HBV replication and gene expression. The expression levels of miR-130a, miR-204 and miR-1236 were always significantly reduced in stable HBV-producing cell lines. (A) Infectious HBV-producing rat hepatoma cell lines Qs2, Qs4, Qs5, and Qs21. Q7 neo is the vector-transfected control cell line. (B) Infectious HBV-producing human hepatoma cell lines UP7-4 and UP7-7. HepG2 neo is the vector-transfected control cell line. *p<0.05. (C) Intracellular HBV replication in HepG2 cells were reduced by cotransfection (coTf) of an HBV ayw genomic dimer plasmid and various miRNA expression vectors using Southern blot assay. The probe used here is a 2.8 kb HBV specific DNA fragment containing HBV core gene. Empty vector DNA and miR-31 were included as negative controls. HBV replicative intermediates: RC relaxed circle, DL double-strand linear, SS single-strand viral DNA. (D) Reduction of HBV precore and pregenomic RNA (3.5 Kb) and envelope-specific mRNA (2.4/2.1 Kb) was detected by cotransfection with miR130a and Northern blot analysis. (E) Reduction of HBV core protein (HBc) was detected by cotransfection with miR-130a and miR-1236 via Western blot analysis. (F) is a chart showing co-transfection of HBV DNA with human miR-130a reduces the secretion of HBsAg and HBeAg in the media of HepG2 as determined by ELISA. No reduction of HBsAg and HBeAg secretion was observed in cells co-transferred with HBV DNA and miR-31. (*P<0.05).
Figure 1:
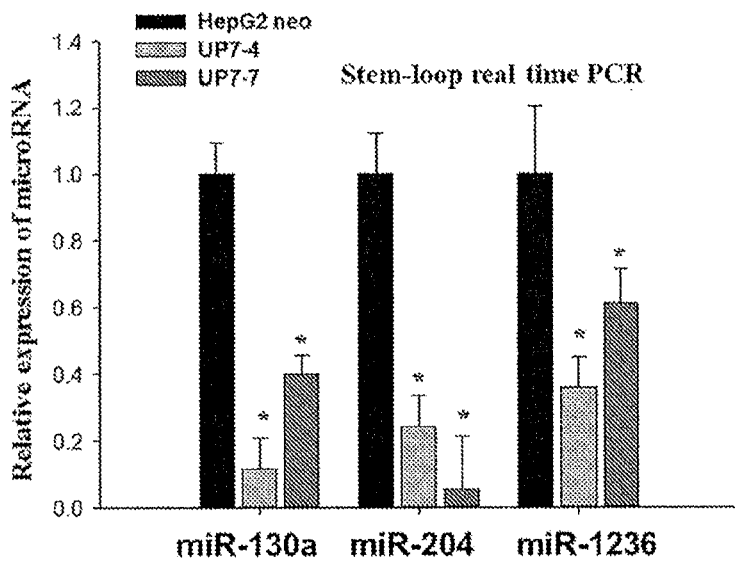
Figure 1:
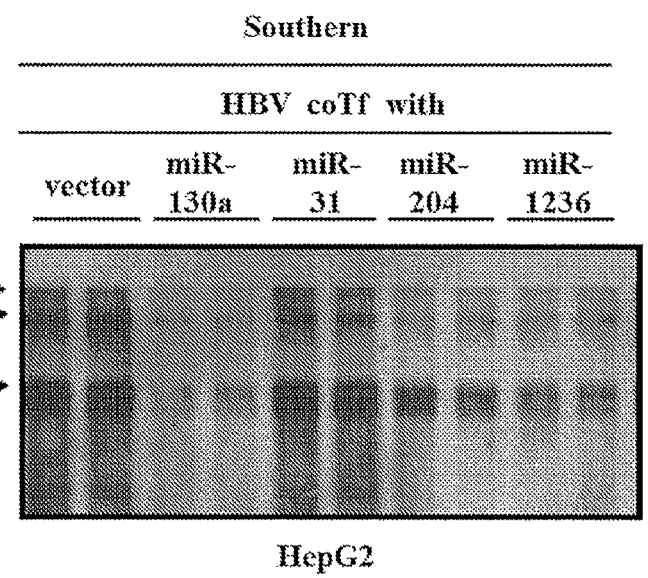
Figure 1:
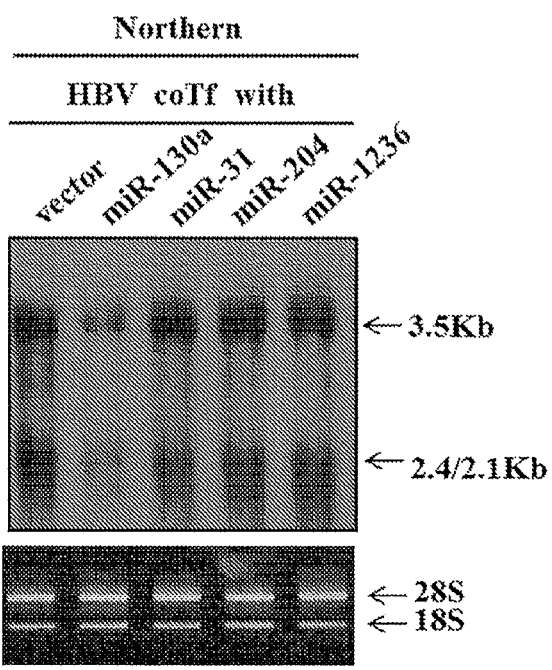
Figure 1:
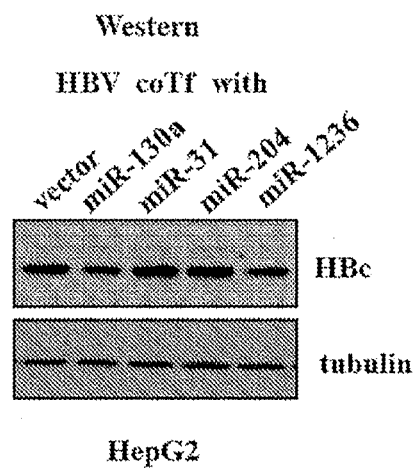
Figure 1:
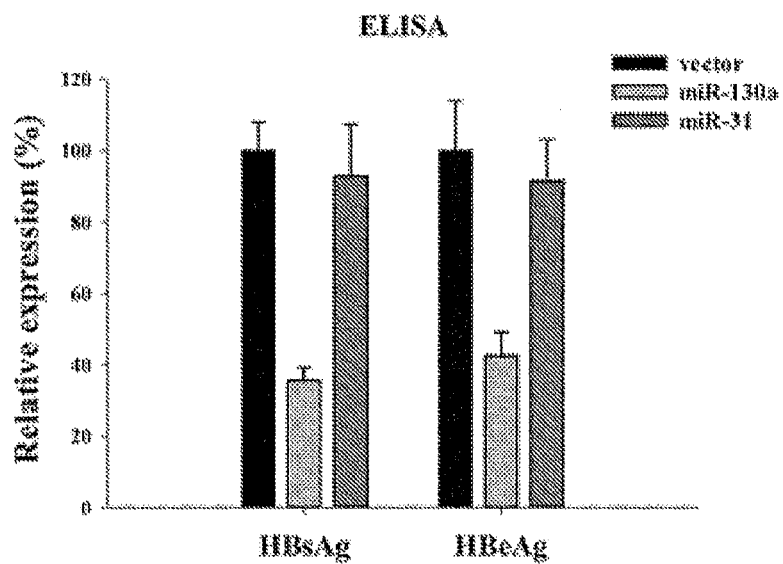

The methods to construct the miRNA expression vectors are as detailed elsewhere. Chen, H. L. et al. *PloS one* 7, e34116 (2012). PCR products were sub-cloned from TA cloning vector (RBC) to pSuper (OligoEngine, Inc) by Hind III digestion. All plasmids were confirmed by sequencing. Approximately 8-400 fold higher level of microRNA expression was detected by transfection and stem loop RT-PCR analysis. MiR-31 was used as a negative control since it had no effect on HBV replication (FIG. 1). The PPARγ and PGC1α expression vectors were from GeneCopoeia.

Source of Antibodies

Anti-HBc (Dako), anti-PPARγ (Santa Cruz), anti-GAPDH, anti-PKLR, anti-G6Pase, anti-tubulin, anti-PGC1α (Origene), anti-PCK1 (Abnova), anti-GCK (Biovision), Secondary antibodies include mouse anti-rabbit-HRP, goat anti-mouse-HRP (GeneTex, Taiwan) and donkey anti-goat-HRP (Santa Cruz).

Synthetic RNA

The synthetic miRNAs (Genepharma) used in FIG. 8 are RNA duplexes without modifications. The sense strand is the same as the mature form of miRNAs. Mimic miR-130a (CAGUGCAAUGUUAAAAGGGCAU (SEQ ID NO:1)), mimic miR-204 (UUCCCUUUGUCAUCCUAUGCCU (SEQ ID NO:3)), mimic miR-1236 (CCUCUUCCCCUUGUCUCUCCAG (SEQ ID NO:4)), mimic negative control (UUCUCCGAACGUGUCACGUTT (SEQ ID NO:75)). The siRNA oligo against PGC1α was from Dharmacon.

MiR-130a Sponge

Each sense and antisense oligos (see Table 1 above) were designed to contain four copies of synthetic target sites of miR-130a. Annealed oligo product was gel purified before PCR amplification. Gel-purified PCR product was sub-cloned into DsRedC1 vector at Hind III site. Colonies were screened by PCR and the orientation of the insert and the copy numbers of target sites were confirmed by sequencing.

Cell Culture

Human hepatoma Huh7 and HepG2 cells were maintained as described previously Chua, P. K., et al. *Journal of virology* 84, 2340-2351 (2010), Le Pogam, S., et al., *Journal of virology* 79, 1871-1887 (2005). In general, the phenotype of viral replication and the effect of microRNA are stronger in HepG2 than Huh7 cells. However, Huh7 cells are easier to passage and transfect. Therefore, we used these two cell lines interchangeably.

PPARγ Agonist and Antagonist

Rosiglitazone and GW9662 were from Sigma. HepG2 and Huh7 cells were seeded in 6-well tissue culture plates at 5×10, Quasdorff, M. et al. *Journal of viral hepatitis* 17, 527-536 (2010) cells/well. At 24 h post-transfection, Rosiglitazone or GW9662 in 0.1% DMSO was added to medium. Culture medium was changed ever two days before harvest.

Measurement of Glucose Production

The glucose level of HBV transgenic mice was measured using a kit of DRI-CHEM SLIDE GLU-PIII (FUJIFILM, JAPAN). Ten microliters of mouse serum was deposited on a FUJI DRI-CHEM SLIDE GLU-PIII. Glucose oxidase (GOD) catalyzes the oxidization of sample glucose to generate hydrogen peroxide which then reacts with dye precursors and forms red dye. The optical reflection density was measured at 505 nm by the FUJI DRI-CHEM analyzer and converted into the glucose concentration (mg/L). For the measurement of glucose concentration in cell culture, HBV producing cells (HepG2 and Q7 cells) were treated with PPARγ antagonist, GW9662 at indicated concentrations. Twenty-four hours before glucose measurement, the medium was replaced with 1 ml of glucose-free DMEM, supplemented with 2 mM sodium pyruvate. After 16 hrs incubation, 50 μl of medium was collected and the glucose concentration (mM) was measured using the glucose colorimetric assay (Biovision).

Quantitative Real-Time PCR

Briefly, 2 μg of total RNA was reverse transcribed into cDNA using random primers and High Capacity cDNA Reverse Transcription kit (Applied Biosystem) at 37° C. for 120 minutes. The cDNA product was then diluted 100 times for real-time PCR analysis using Power SYBR Green PCR master mix (Applied Biosystem), and the default condition in a 20 μl reaction volume by Applied Biosystems 7500 Real-Time PCR System. Data were analyzed by relative quantification methods (ΔΔCt methods) using 7500 software V2.0.1.

Stem-Loop qCR for miRNA

Taqman RT and stem-loop real-time assay were from Applied Biosystems: miR-31 (assayID: 002279), miR-130a (assayID: 000454), miR-204 (assayID: 000508) and miR-1236 (assayID: 002752). Briefly, 100 ng RNAs were reverse transcribed by specific stem-loop primer and further analyzed by Taqman real-time PCR assay using default setting. U6 snRNA (assayID: 001973) was used as an internal loading control. Data were analyzed by Applied Biosystems 7500 software V2.0.1.

Southern and Northern Blot

HBV core particle-associated DNA, total cellular cytoplasmic RNA, and microRNA were analyzed by Northern blot as described previously. Chua, P. K., et al. *Journal of virology* 84, 2340-2351 (2010), Le Pogam, S., et al., *Journal of virology* 79, 1871-1887 (2005).

Luciferase Reporter Assay

Assay for 3' UTR or enhancer/promoter was as described previously. Chen, H. L., et al., *PloS one* 7, e34116 (2012).

Native Agarose Gel Electrophoresis and Western Blot

Native agarose gel electrophoresis and Western blot for detecting HBV core particles as shown in FIG. 5 were as described. Chua, P. K., et al. *Journal of virology* 84, 2340-2351 (2010), Stable miR-130a Expressing Cell Lines Approximately one million Huh7 and HepG2 cells were transiently transfected by 3 µg plasmid DNA (pSuper and pSuper-miR-130a) with Polyjet (SignaGen), followed by G418 selection for three weeks. The G418-resistant colonies were pooled together.

LNA-miR-130a Knockdown

HepG2 and Huh7 cells were cotransfected with puromycin resistamt plasmid (pTRE2pur) and LNA-scramble control or LNA anti-miR-130a (Locked Nucleic Acid, Exiqon), using Lipofectamine 2000 (Invitrogen). Twelve hours post-transfection, transfected culture was treated with puromycin (2 µg/ml) for 2 days, followed by reduced concentration of puromycin (0.5 µg/ml) for another 2 days before harvesting for Western blot analysis. Chen, H. L., et al., *PloS one* 7, e34116 (2012).

Bioinformatic Analysis.

Computer-based programs including Targetscan (http://www.targetscan.org/), Pictar (http://pictar.mdc-berlin.de/), Microinspector (http://bioinfo.uni-plovdiv.bg/microinspector/), RNAhybrid (http://www.bibiserv.techfak.uni-bielefeld.de/) and DIANA (http://diana.cslab.ece.ntua.gr) were used to predict potential targets for miR-1236, miR-130a and miR-204. The minimal free energy of binding less than −20 kcal/mol was used as the cut-off value.

MicroRNA Taqman Low Density Array Analysis

The total RNA of HBV-producing cells were extracted by Trizol (Invitrogen). The quality and quantity of RNA samples were determined by Agilent 2100 Bioanalyzer using RNA 6000 Nano Kit (Agilent Technologies, Inc.). The reverse transcription reactions were performed using Taq-Man MicroRNA Reverse Transcription kit (Applied Biosystem). The expression of miRNA was detected by TaqMan® Rodent MicroRNA Array A (Applied Biosystems), and analyzed by Applied Biosystems 7900 HT Fast Real-Time PCR System containing 381 rodent miRNA targets.

Statistics

Statistical significance was determined using the Student's t test. In all figures, values were expressed as mean±standard deviation (SD) and statistical significance ($p<0.05$) was indicated by an asterisk. The data represent results from at least three independent experiments.

Animals

The generation of HBV transgenic mice on an ICR background has been reported previously. Chen, C. C. et al. *Gene therapy* 14, 11-19 (2007). The transgene is a 1.3-fold HBV genome (genotype D, serotype ayw). The Tg[HBV1.3] mouse line was used in this study. All animals were housed in a specific-pathogen-free environment in the animal facility of the Institute of Biomedical Sciences, Academia Sinica.

RNase Protection Analysis (RPA)

RPA was performed using the vendor's protocol (RPA III, Ambion). A 392 nt antisense riboprobe was radiolabelled by in vitro transcription using a NotI linearized DNA fragment from a pGEM-T vector containing HBV sequences nt 2150-1820. The protected pgRNA fragment was 330 nt in length. HBV polymerase mutant Y63D is defective in DNA synthesis but competent in pgRNA encapsidation. Ning, X. et al. *PLoS pathogens* 7, e1002255 (2011). This mutant accumulates a higher level of encapsidated pgRNA in the core particles due to its arrested nucleotide priming of DNA synthesis.

MiR-130a Promoter Analysis by Deletion Mapping

An upstream fragment of the miR-130a precursor (−750 to −1 nt), containing putative binding sites for NF-κB/p65, Egr-1, and CREB, was amplified by PCR from human HepG2 genomic DNA. PCR primers were as listed in Table 1. The PCR products were separated by agarose gel electrophoresis, and the isolated DNA fragments were then cloned into the restriction enzyme digested pGL3 Basic Vector (Promega, Madison, Wis.) containing a firefly luciferase reporter (New England Biolab, Ipswich, Mass.). Various promoter deletion plasmids, containing shorter fragments upstream from the miR-130a precursor, were derived from the full-length promoter plasmid by PCR amplification and cloning using various PCR primers (Table 1 above). All the promoter plasmids were confirmed by sequencing. HuH-7 cells were transfected with promoter deletion plasmids for 48 hrs and firefly luciferase activities were then measured and normalized to each cotransfected renilla luciferase level. The full-length 3'UTRs of PPARγ, PGC1α and SP1 were amplified from genomic DNA of HepG2 cells using their respective forward and reverse primers (Table 1), and cloned into a psiCHECK-2 luciferase vector (Promega, Madison, Wis.) (Shih, C. et al. Virology 179, 871-873 (1990)). Target site mutants containing altered sequences at PGC1α 3'UTR and a miR-130a mutant containing altered seed sequences, were engineered by using paired mutant primers (Table 1) and Site-directed Mutagenesis kit (Stratagene, Santa Clara, Calif.).

Results

Identification of Three Anti-HBV Cellular microRNAs

Two different approaches, including microRNA microarray (Table 2) and bioinformatic analysis (Table 3), were performed to identify potential anti-HBV cellular miRNA.

TABLE 2

Q-PCR microarray of cellular microRNAs in HBV-producing and control hepatoma cell lines
Fold change §

| miRNA | Qs2 | Qs4 | Qs5 | Qs21 | average |
|---|---|---|---|---|---|
| rno-miR-222 | −34267 | −32467 | −16233 | −32467 | −25974 |
| rno-miR-10a | −645.16 | −465.12 | −141.44 | −518.13 | −314.96 |
| rno-miR-204* | −383.14 | −281.69 | −301.2 | −324.68 | −310.47 |
| rno-miR-187 | −167.22 | −119.33 | −125.31 | −139.28 | −135.50 |
| rno-miR-342 | −110.90 | −86.96 | −88.50 | −97.09 | −96.53 |
| rno-miR-31 | −78.74 | −37.31 | −25.13 | −121.36 | −45.69 |
| rno-miR-181a | −34.13 | −25.64 | −25.64 | −29.33 | −28.29 |
| rno-miR-196c | −10.38 | −13.09 | −12.03 | −11.57 | −11.69 |
| rno-miR-9 | −15.92 | −12.70 | −13.73 | 1.69 | −10.15 |
| rno-miR-202-3p | −9.91 | 1.89 | −9.99 | −7.83 | −7.40 |
| rno-miR-195 | −8.62 | 1.44 | −9.13 | −8.74 | −6.26 |
| rno-miR-130a* | −4.67 | −3.86 | −8.33 | −7.63 | −5.52 |

Qs2, Qs4, Qs5, and Qs21 are infectious HBV-producing rat hepatoma cell lines. Shih, C. H., et al. *Proceedings of the National Academy of Sciences of the United States of America* 86, 6323-6327 (1989), Shih, C., et al. *Virology* 179, 871-873 (1990).
§ The fold changes of the expression of miRNA in Qs2, Qs4, Qs5, Qs21 were normalized to the control cell lines Q7 neo.
*The results of miR-204 and miR-130a were confirmed by stem-loop real time PCR analysis using HBV-producing human hepatoma cell lines UP7-4 and UP7-7.

TABLE 3

Computational prediction of cellular microRNAs with a strong potential of binding to HBV RNA pregenome #

| miRNA | Free energy (kcal/mol) | Position @ |
|---|---|---|
| hsa-miR-1236 | −34.9 | nt 1725 |
| hsa-miR-663 | −33.6-31.3 | nt 1526 nt 1563 |
| hsa-miR-1207-5p | −33.0-31.4 | nt 1478 nt 1544 |
| hsa-miR-92b* | −32.7 | nt 1406 |
| hsa-miR-1915 | −31.8 | nt 1425 |
| hsa-miR-638 | −31.7 | nt 1522 |
| hsa-miR-939 | −31.4 | nt 1523 |
| hsa-miR-744 | −31.2 | nt 1329 |
| hsa-miR-663b | −30.0 | nt 1591 |

The entire miRbase version 16.0 were screened with HBV (ayw) 3'UTR sequences (nt 1521-2122) using the Microinspector Program. MiR-1236 was predicted to have the highest degree of free energy of binding. Galibert, F., et al. *Nature* 281, 646-650 (1979).
@ The positions refer to the first nucleotide of microRNA binding sites on HBV ayw genome.

HBV-producing hepatoma cell lines that produce virions infectious in chimpanzees were established previously. Shih, C. H., et al. *Proceedings of the National Academy of Sciences of the United States of America* 86, 6323-6327 (1989), Shih, C., et al. *Virology* 179, 871-873 (1990). MicroRNA expression profiles between stable HBV-producing and control cell lines were compared by the qPCR microarray described above. Significant reduction of at least a dozen miRNAs was observed in HBV-producing cells (Table 2). The reduction of these miRNAs from microarray study was validated by stem-loop qPCR analysis (FIG. 1A). The results suggest that these miRNAs could have an anti-HBV effect which may explain their reduced expression levels in several independently established rat and human HBV-producing cell lines.

Cotransfection and viral replication assays were performed to screen anti-HBV microRNAs from those listed in Table 2. miR-204 and miR-130 were identified as candidate anti-HBV microRNAs.

In another approach, miR-1236 was identified as an anti-HBV microRNA by the Microinspector target-prediction algorithm. This miRNAs can bind to HBV genome with the highest free energy (−34.9 kcal/mol) (Table 3).

Viral Replication and Gene Expression Attenuated by miR-130a, miR-204, and miR-1236

As shown in FIG. 1B, miR-130a, miR-204, or miR-1236 each inhibits HBV DNA replication in human hepatoblastoma HepG2 cells. Intracellular HBV replication in HepG2 cells were reduced by cotransfection (coTf) of an HBV ayw genomic dimer plasmid and various miRNA expression vectors using Southern blot assay (FIG. 1C). Northern blot analysis (FIG. 1D) of total cytoplasmic RNA from the cotransfected culture revealed that miR-130a reduced the level of HBV pregenomic RNA (pgRNA). Neither miR-204 nor miR-1236 had any apparent effect on pgRNA.

Next, the effects of these microRNAs on HBV protein expression, including core protein (HBc), surface antigen (HBsAg) and e antigen (HBeAg), were examined. miR-130a and miR-1236, but not miR-204, were found to reduce HBV protein expression in HepG2 cells (FIGS. 1E and F).

MiR-1236 Targets HBV Directly

Figure 2:
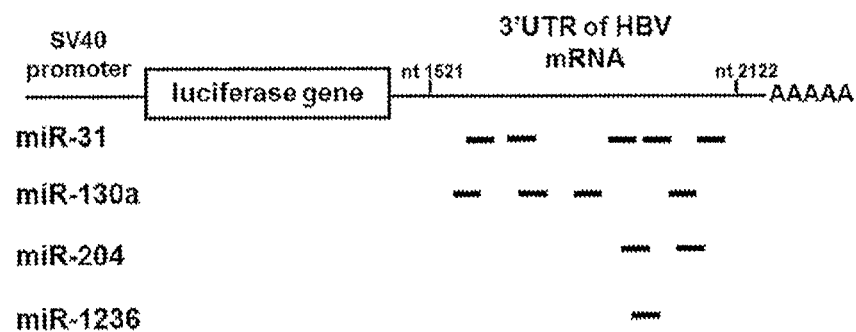
FIG. 2 is a diagram showing that miR-1236 directly targets HBV specific RNA. (A) upper panel: Potential microRNA target sites on HBV ayw genome were predicted by different computer algorithms. lower panel: Huh7 cell were cotransfected with a luciferase reporter plasmid containing HBV nt 1521-2122 and various miRNA expression vectors (Materials and Methods). Only miR-1236 displayed significant reduction of luciferase activity (*p<0.05). (B) By compensatory mutagenesis, miR-1236 was shown to target HBV genome directly. upper panel: Sequence alignment of wild type and mutant miR-1236 (SEQ ID NOs: 4 and 6, respectively) with putative target sites on wild type or mutant HBV genomes (nt 1724-1755; SEQ ID NO:5 and SEQ ID NO:7, respectively). Mutation sites were underlined. lower panel: Huh7 cells were cotransfected with wild type or mutant pGL3-HBV 3' UTR (nt1521-2122) reporter and wild type or mutant miR-1236 expression vector. Reduction in firefly luciferase activity was restored when mutant miR-1236 was matched with the mutant reporter (*p<0.05). (C) A summary of the differential effects from three putative anti-HBV miRNAs on the levels of HBV DNA, RNA, protein, and luciferase activity in 3' UTR reporter assay.
Figure 2:
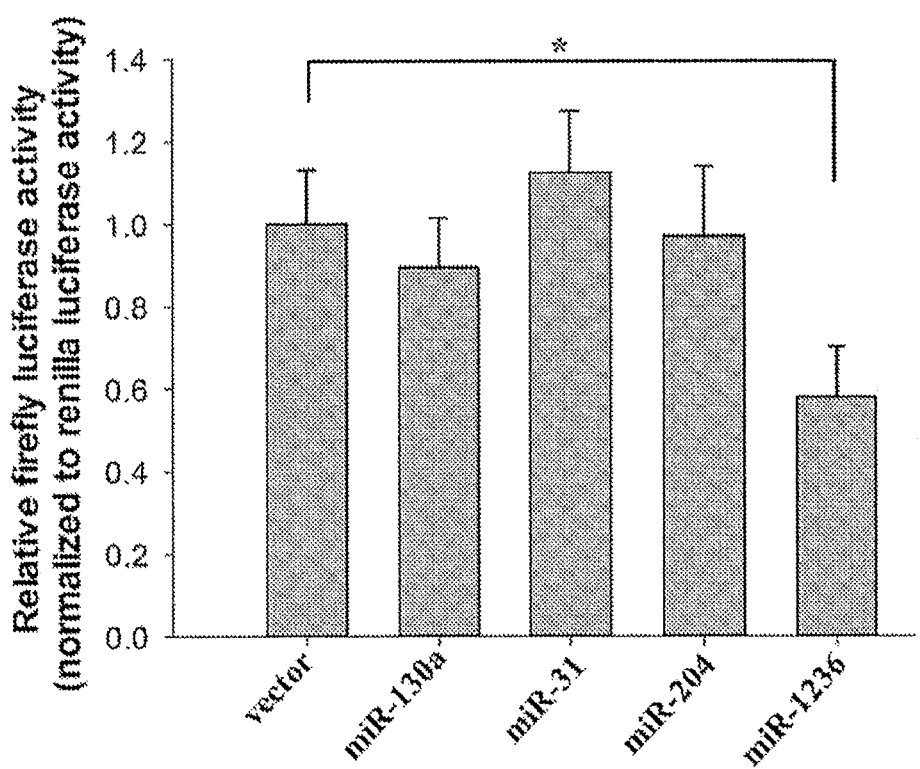
Figure 2:
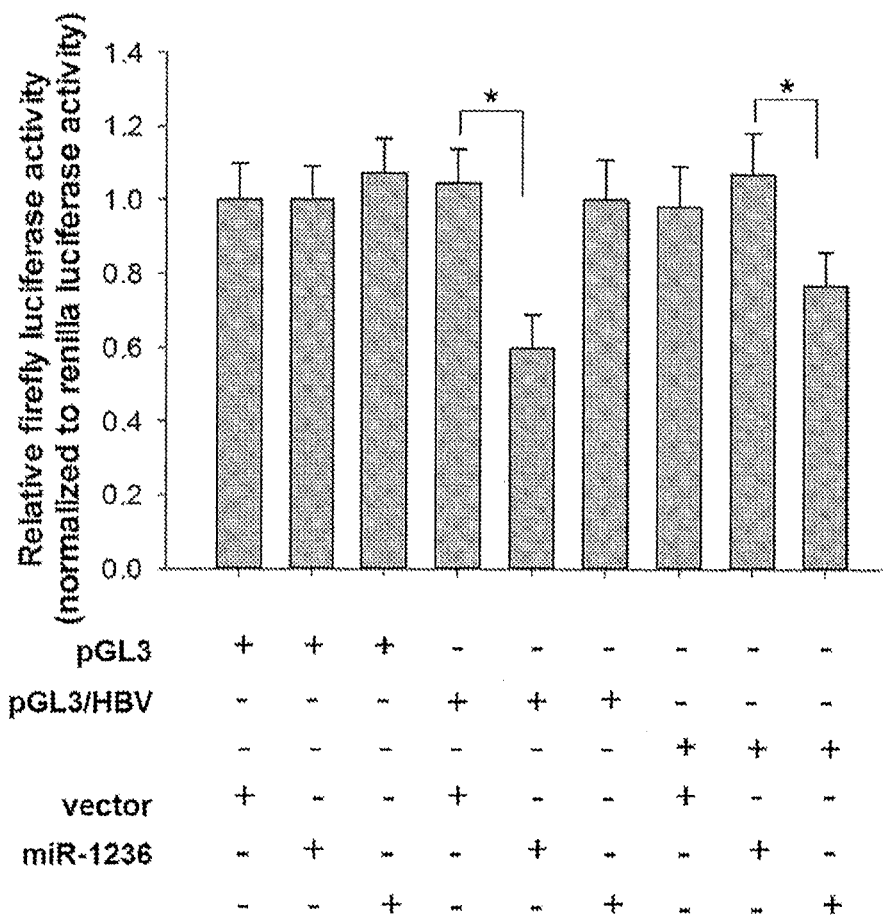

Bioinformatic analysis predicted potential target sites of miR-1236, miR-204, and miR-130a clustering between nt 1521 and nt 2122 of HBV ayw genome, Galibert, F., et al. *Nature* 281, 646-650 (1979). (FIG. 2A). This region coincides with the 3'UTR of HBsAg, HBeAg and HBc specific RNAs as well as the polymerase coding region of pgRNA, Tiollais, P., et al., *Nature* 317, 489-495 (1985). A 3' UTR luciferase reporter assay were performed to determine the activity of the microRNAs in regulating gene expression via the predicted targeting site and miR-1236 was found to significantly reduce the luciferase activity (FIG. 2A).

To test further whether miR-1236 can directly bind to its single predicted target site of HBV, a compensatory mutagenesis assay was performed by introducing mutations into the seed sequences of miR-1236 and its target site of HBV (FIG. 2B). This seed sequence mutant of miR-1236 did not reduce the reporter activity containing the wild type HBV 3'UTR sequences. Similarly, wild type miR-1236 had no effect on HBV 3'UTR containing the target site mutation. However, the combination of seed mutant miR-1236 and the target site mutant restored the inhibitory effect of miR-1236 on the reporter activity (FIG. 2B). This result indicates a direct interaction between miR-1236 and HBV. FIG. 2C summarizes the effects of miR-1236, miR-130a, and miR-204 on HBV DNA, RNA, protein, and 3' UTR reporter assay.

Reduction of Endogenous miR-130a Enhanced HBV DNA Replication and Protein Expression.

Figure 3:
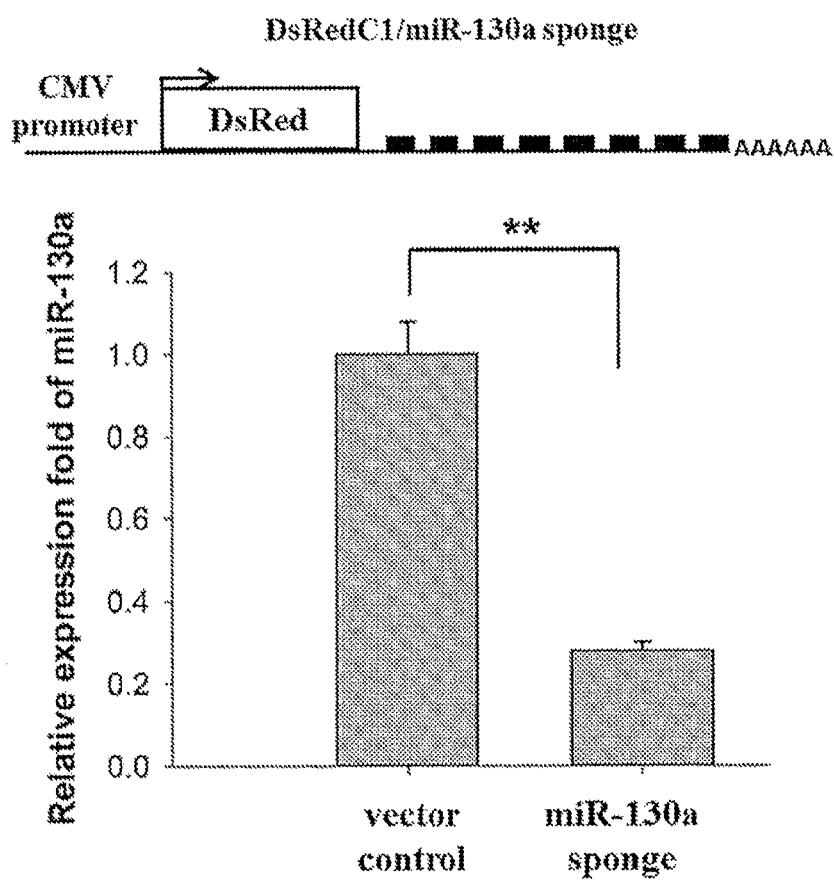
FIG. 3 is a diagram showing that miR-130a attenuated HBV DNA replication and protein expression by targeting two major metabolic regulators—PGC1α and PPARγ in hepatocytes. (A) upper panel: A cartoon of the miR-130a sponge plasmid. Lower panel: The reduction of endogenous miR-130a by sponge treatment was measured by stem-loop qPCR. (B) Upper panel: HBV DNA replication was stimulated by the cotransfected sponge by Southern blot with an HBV specific probe. (C) HBV DNA replication was enhanced by LNA-miR-130a treatment which can antagonize the endogenous miR-130a. HepG2 cells were cotransfected with HBV DNA and LNA-miR-130a or a scramble control at indicated concentrations. (D) is a chart showing the relative expression of endogenous hsa-miR-130a at different doses of LNA-miR-130a in HepG2 cells, which was measured by stem-loop real-time PCR. U6 snRNA was used as an internal control. (*p<0.05). (E) is a chart showing the co-transfection of HBV DNA with LNA-miR-130a antagomir enhanced secretion of HBsAg and HBeAg in a dose-dependent manner in HepG2 cells by ELISA. (*p<0.05). (F) is a chart showing the co-transfection of HBV DNA with LNA-miR-130a antagomir increased the HBc protein level in a dose-dependent manner in HepG2 cells by Western blot assay using an anti-HBc antibody. (G) This diagram hypothesized two possible triad relationships among the host factor, miR-130a, and HBV. (H) MiR-130a, but not miR-204, can reduce the activity of HBV enhancer II in Huh? cells. HBV enhancer II-containing reporter (pGL3/enhII) was cotransfected with various miRNA expression vectors or vector control (Materials and Methods). pGL3/enhII (−) was a negative control carrying an HBV enhancer II in an antisense orientation.*p<0.05. (I) Expression of miR-130a precursor and its mature form was detected by Northern blot analysis in HepG2 cell lines stably transfected with miR-130a expression vector. (J) Concurrent reduction of PGC1α and PPARγ mRNAs in stable miR-130a expressing cell lines was measured by Northern blot analysis. (K) Western blot analysis detected the reduction of PGC1α, and PPARγ proteins in stable miR-130a expressing cells. (L) is a diagram showing the reduction of PGC1α and PPARγ mRNA in stable miR-130a expressing or HepG2 cell lines as measured by RT-qPCR analysis (upper panel). No appreciable difference in the protein levels of SP1, PPAR α, CEBPb, and HNF4 by Western blot analysis (lower panel). (M) Treatment by LNA-miR-130a increased PGC1α mRNA and protein by real time RT-qPCR (L, upper panel) and Western blot analysis (L, lower panel), respectively. (N) is a diagram showing that MiR-130a significantly reduced the luciferase activity in a reporter cotransfection assay of the 3' UTR of PGC1α (NM_013261) and PPARγ (NM_005037), but not the 3' UTR of SP1 (NM_003109). (O) MiR-130a was shown to directly target at the 3' UTR of PGC1α by compensatory mutagenesis. (*p<0.05). Mutation sites were underlined in sequence alignment. SEQ ID NOs:1, 8, 9 and 10 are found from top to bottom, respectively. (P) is a diagram showing the co-transfection of the PGC1α 3'UTR luciferase reporter with increasing amounts of miR-130a resulted in decreasing reporter activity in a dose response manner (upper panel). Conversely, treatment with increasing amounts of LNA-miR-130a plasmid resulted in increasing reporter activity in a dose response manner (lower panel). (Q) is a Southern blot showing PGC1α rescued HBV DNA replication in a dose-dependent manner in stable miR-130a expressing cell lines. (R) is a Western blot showing PGC1α rescued HBV protein expression in a dose-dependent manner in stable miR-130a expressing cell lines. (S) is a diagram showing the depletion of endogenous PGC1α by siRNA treatment resulted in repression of HBV DNA replication and protein expression and HepG2 cells were cotransfected with HBV ayw dimer and siRNA-PGC1α or non-target control at increasing concentrations. Gradually decreased HBV DNA replication was analyzed by Southern blot assay. (T) is a Western blot using anti-HBc antibody showing reduced HBc. At 48 hrs post-transfection, culture media were collected and cells were harvested for total RNA and protein extraction. (U) is a graph showing reduced HBsAg and HBeAg as confirmed by ELISA. (V) is a Western blot showing the efficiency of siRNA treatment for PGC1α. (W)
Figure 3:
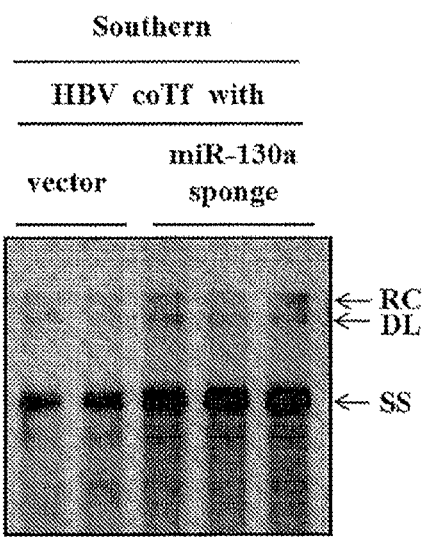
Figure 3:
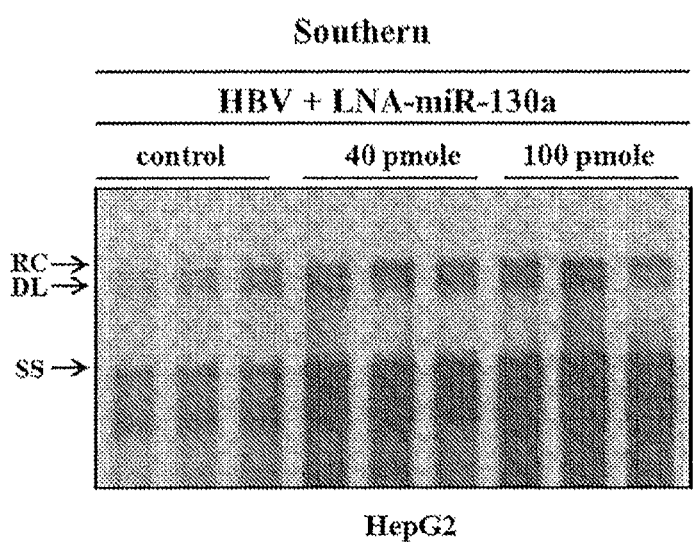
Figure 3:
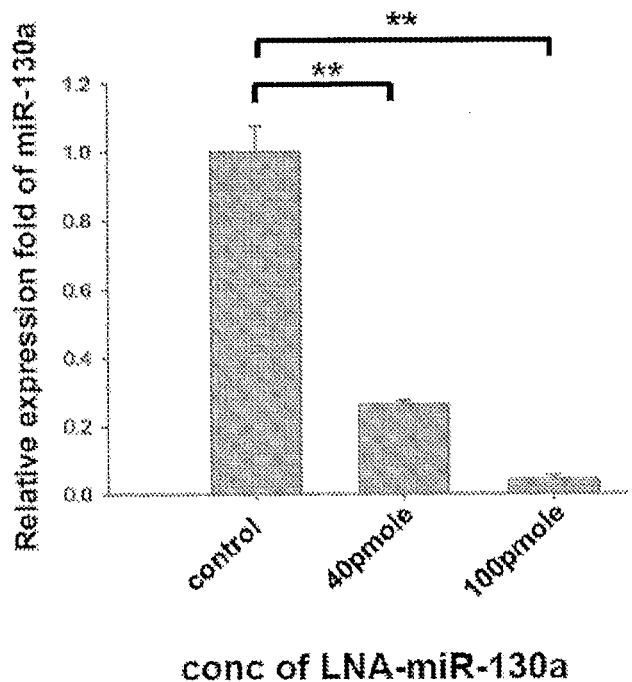
Figure 3:
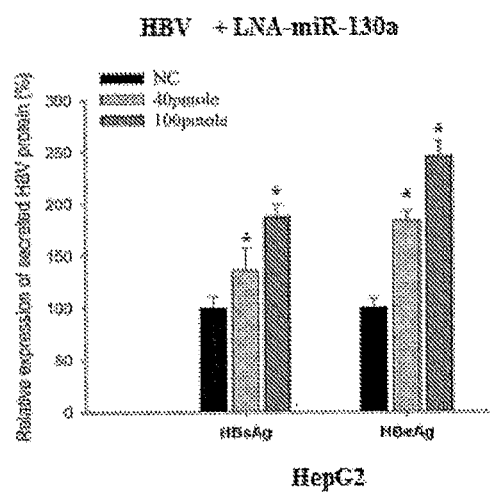
Figure 3:
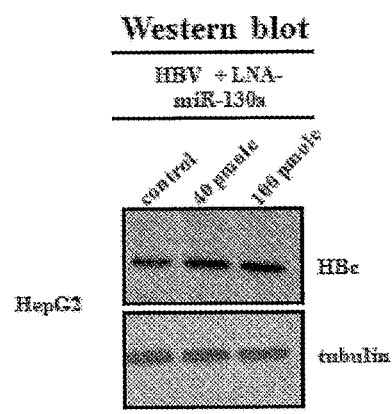
Figure 3:
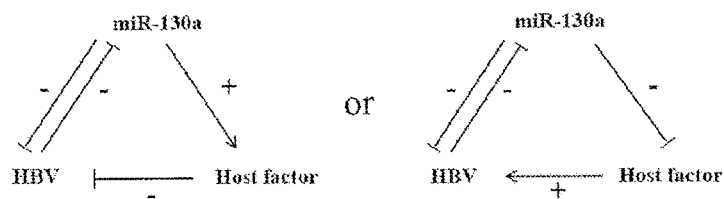
Figure 3:
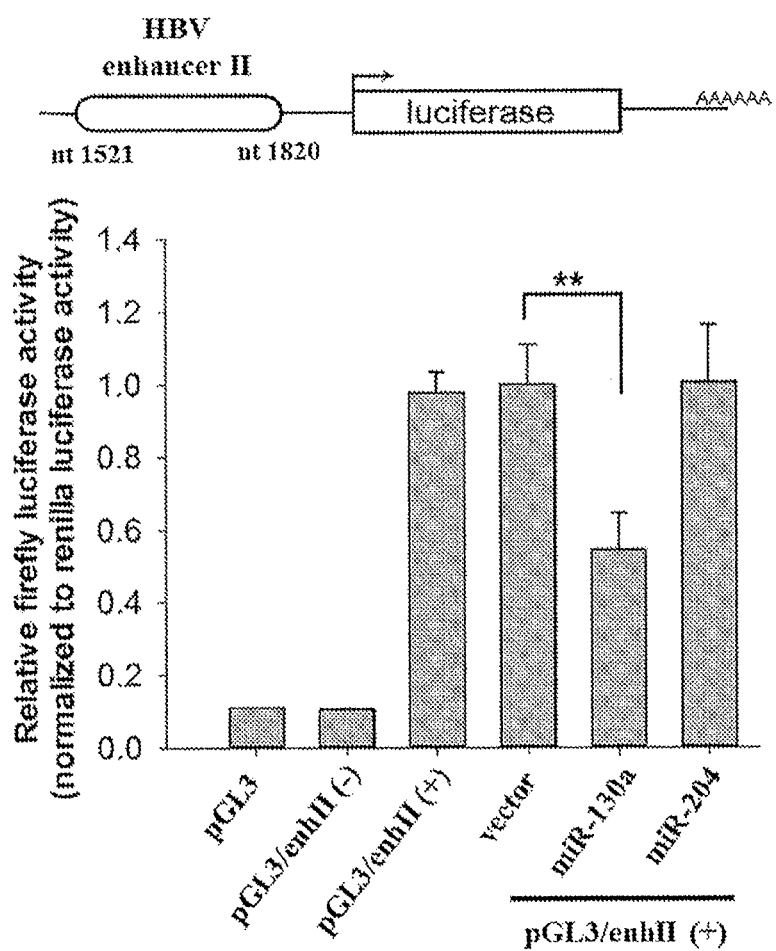
Figure 3:
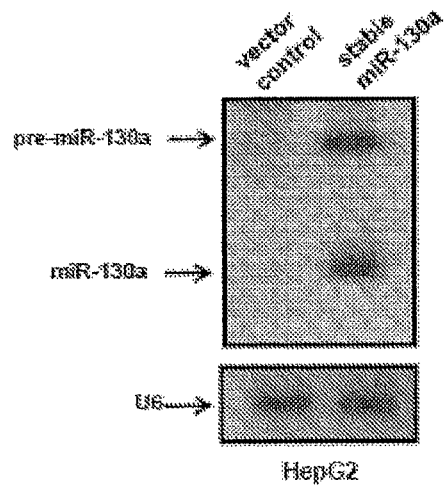
Figure 3:
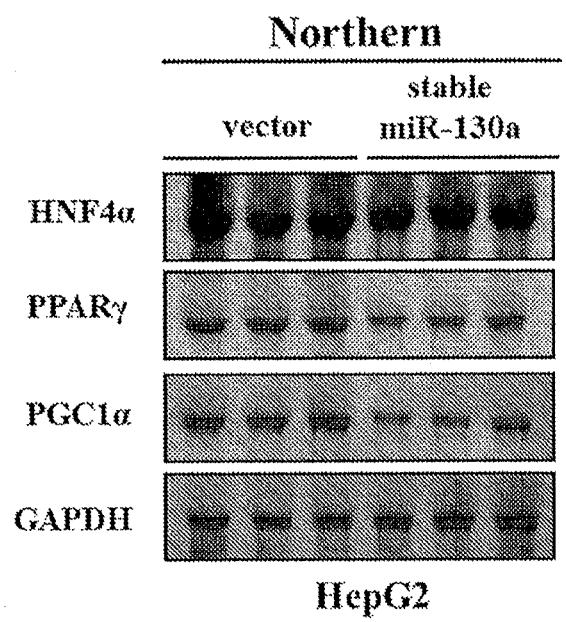
Figure 3:
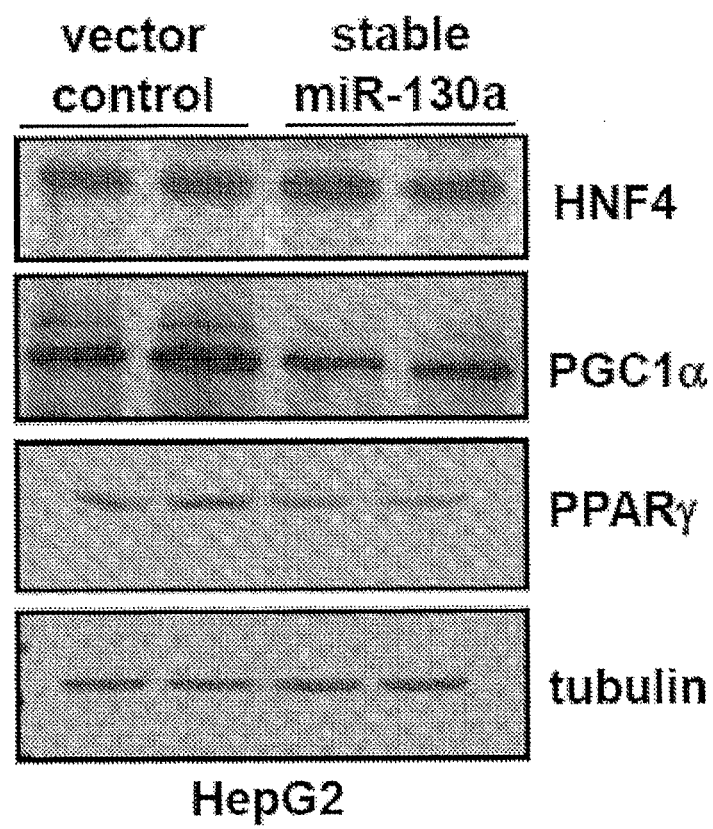
Figure 3:
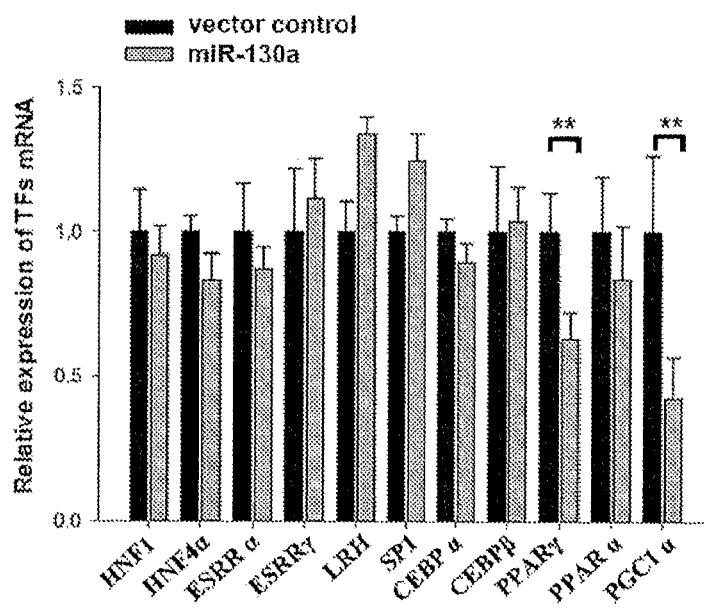
Figure 3:
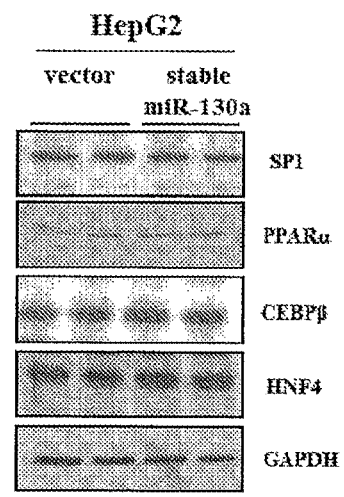
Figure 3:
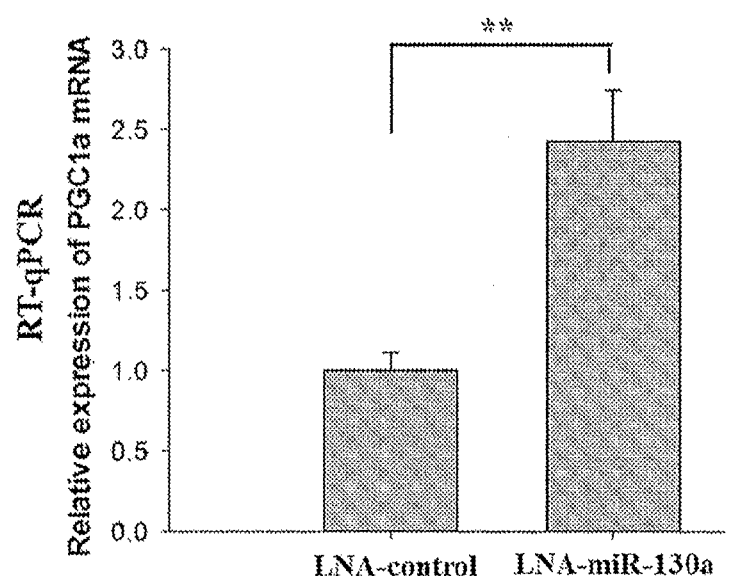
Figure 3:
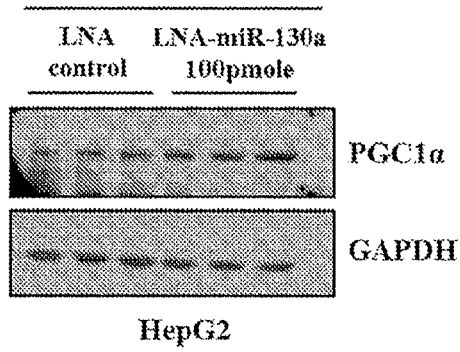
Figure 3:
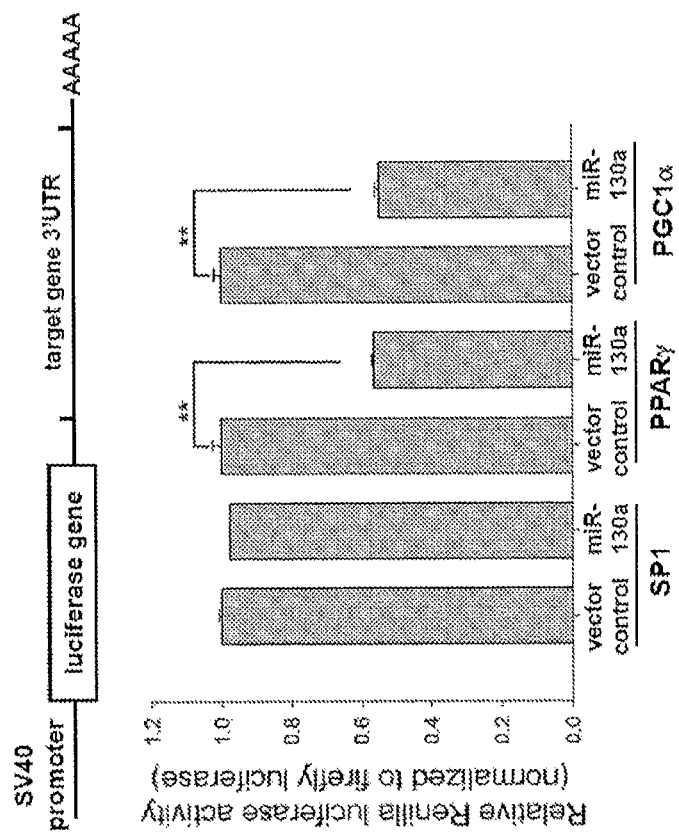
Figure 3:
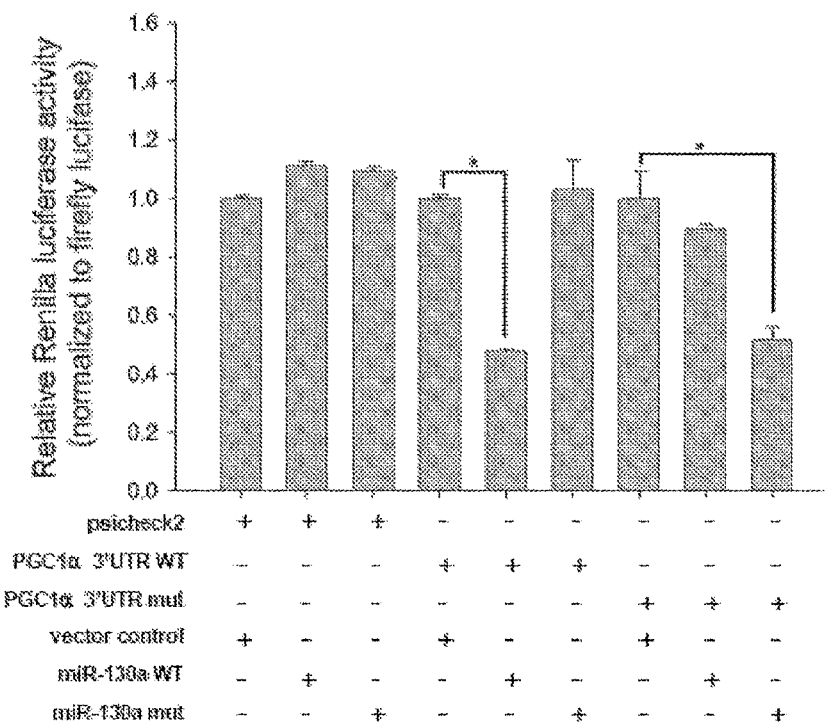
Figure 3:
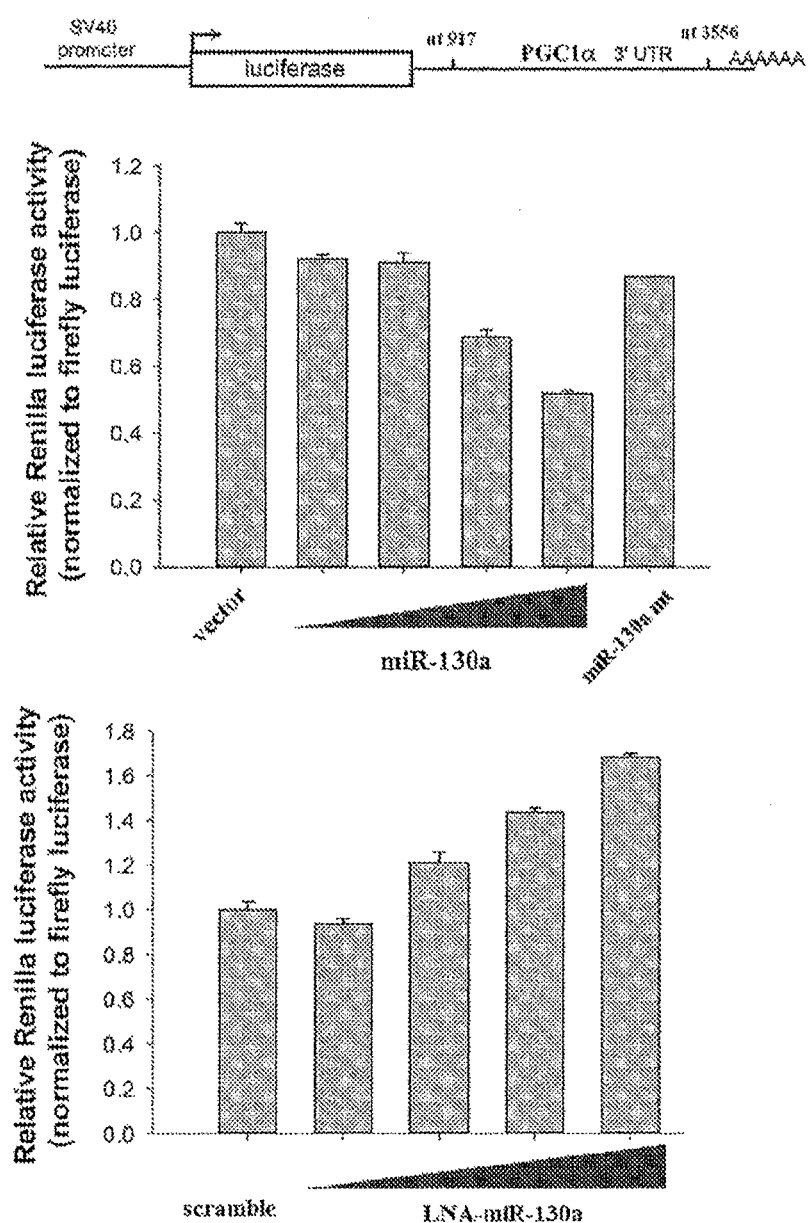
Figure 3:
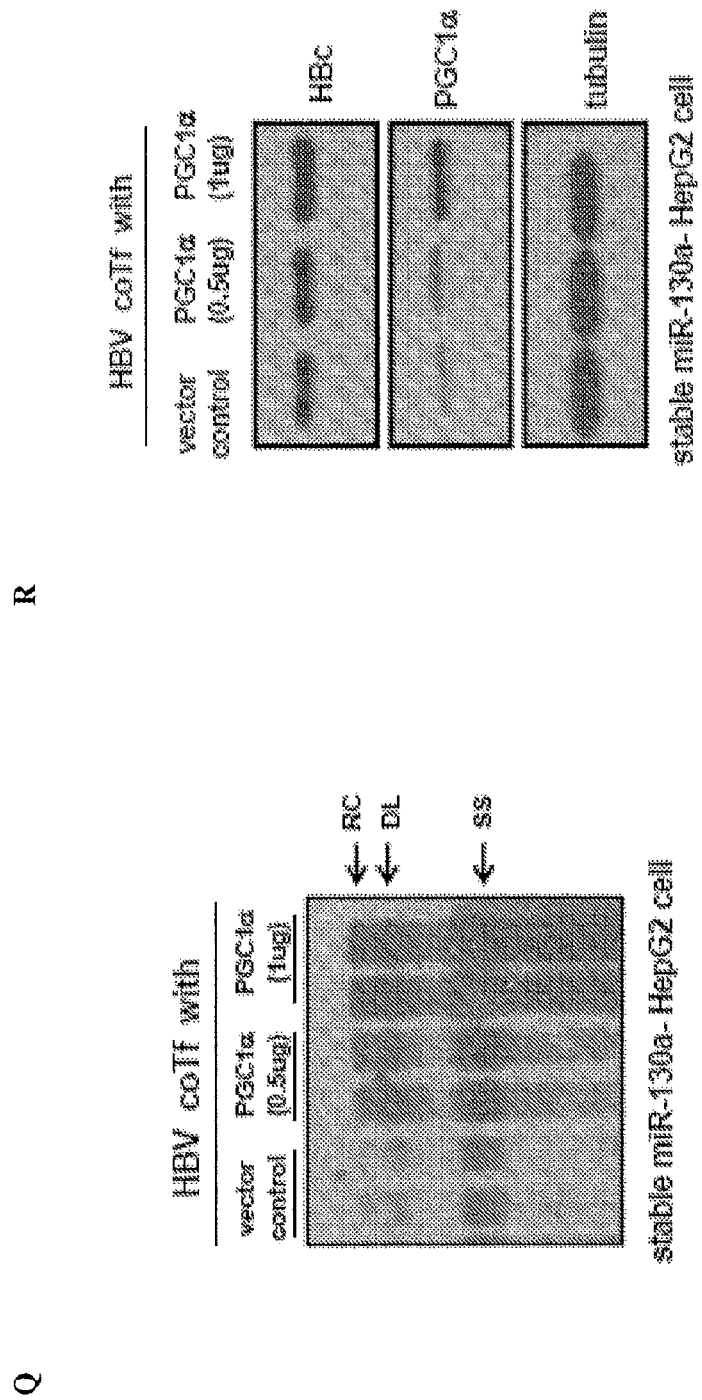
Figure 3:
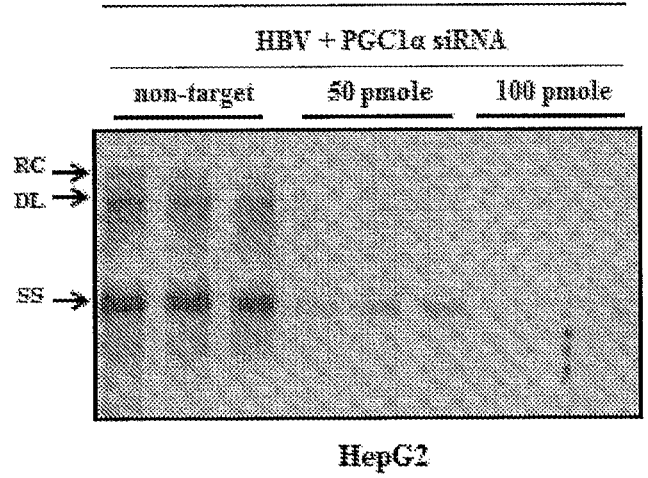
Figure 3:
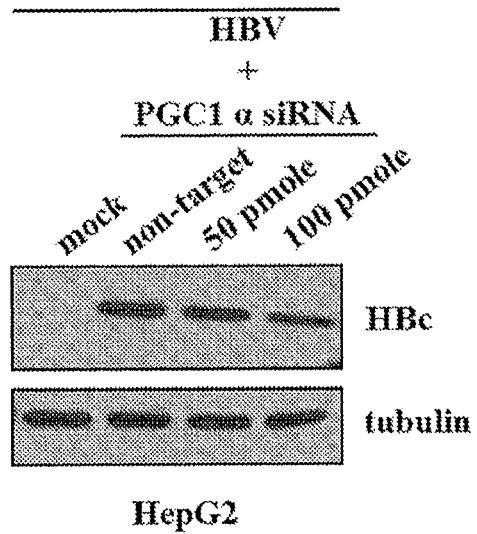
Figure 3:
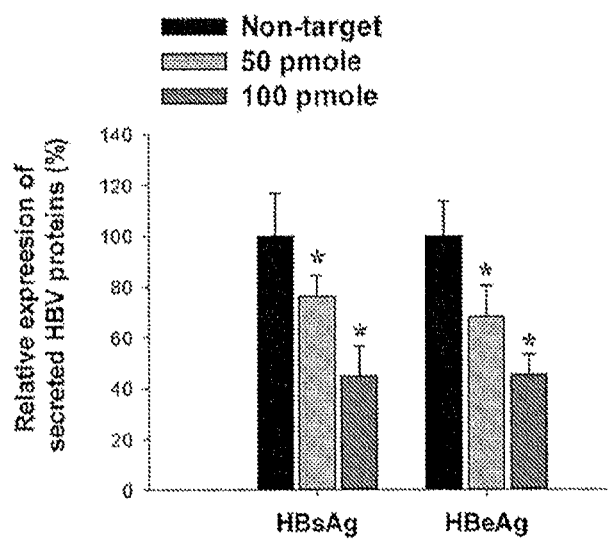
Figure 3:
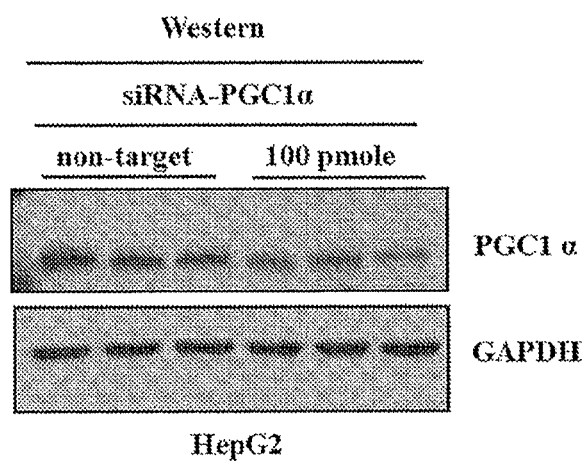
Figure 3:
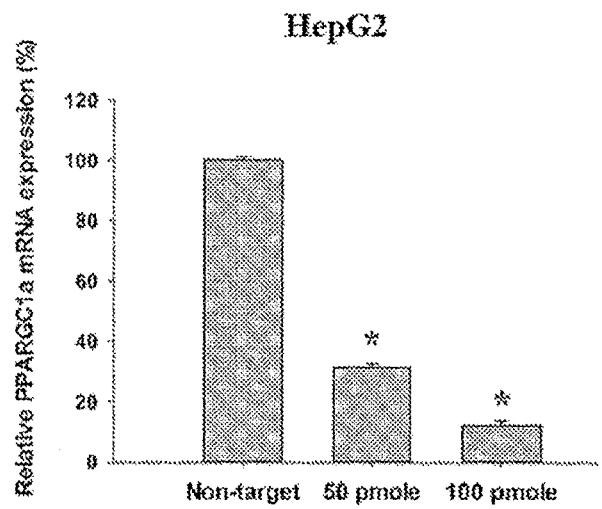
Figure 3:
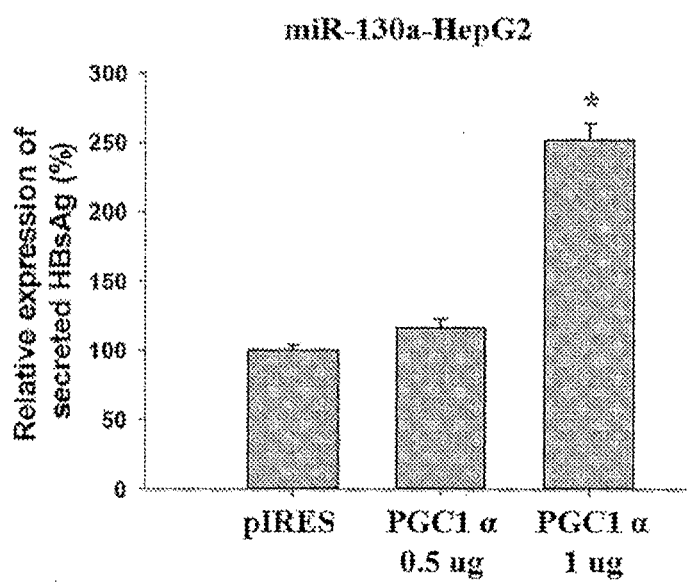
Figure 3:
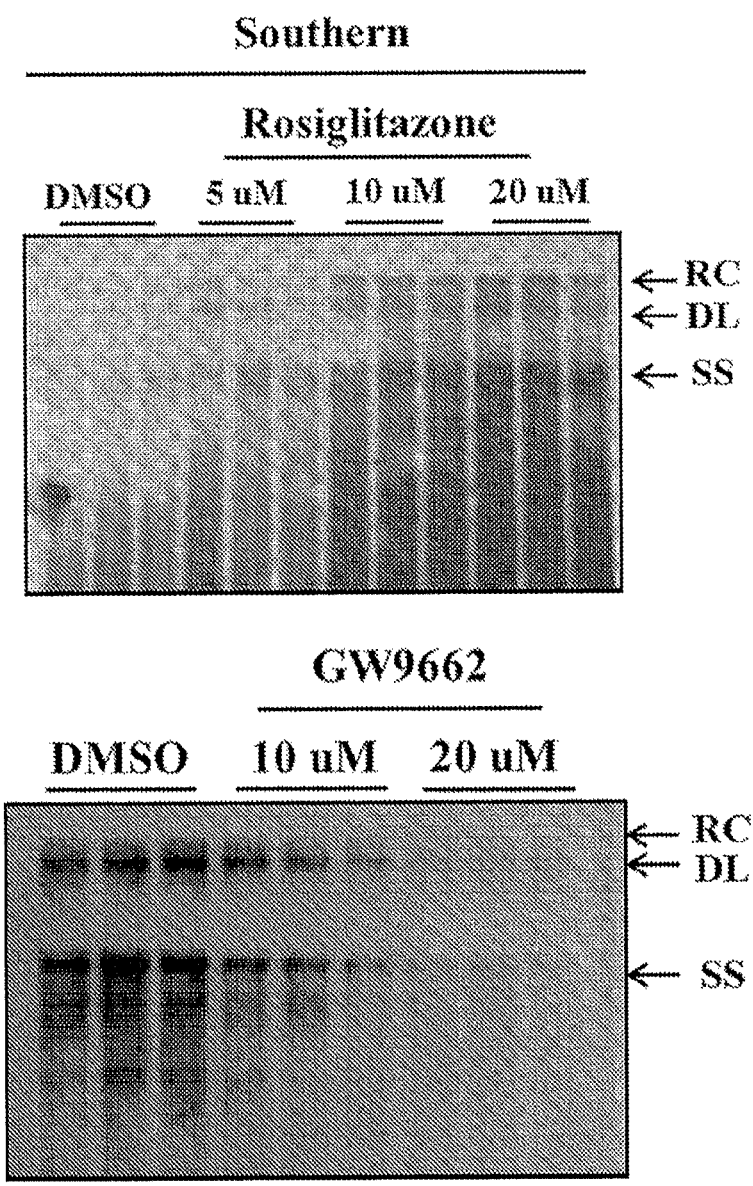
Figure 3:
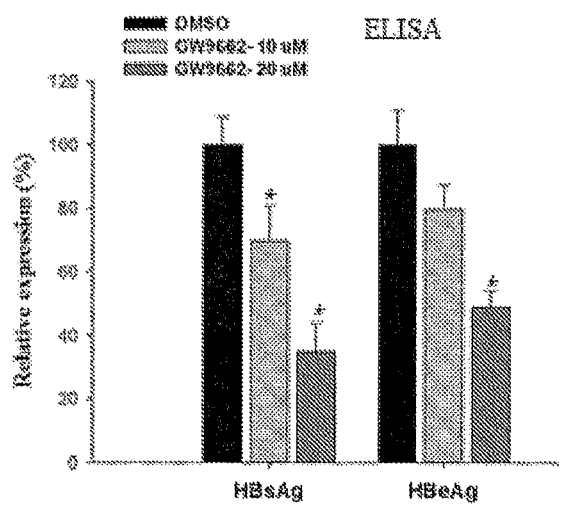

A miR-130a sponge plasmid which contains 8 copies of miR-130a synthetic target site at the 3'UTR of a DsRed reporter gene was constructed to further elucidate the anti-HBV mechanism of miR-130a. This sponge plasmid can efficiently knockdown the endogenous miR-130a in Huh7 cells by stem-loop qPCR (FIG. 3A). Cotransfection of this sponge plasmid with HBV genome significantly increased viral DNA replication (FIG. 3B) and protein synthesis. Similar results were obtained when the endogenous miR-130a was reduced by treatment with LNA-miR-130a antagomir (FIGS. 3C, 3D, 3E and 3F).

MiR-130a can Knockdown HBV RNA Indirectly

Since the reporter assay detected no appreciable effect from miR-130a and miR-204 (FIG. 2A), these two microRNAs probably attenuated HBV replication via an indirect mechanism, rather than by direct binding to HBV specific RNA like miR-1236. As suggested in FIG. 3G, miR-130a could reduce HBV replication by targeting a third party host factor positively or negatively, which in turn could act on HBV negatively or positively. The host factor might be a transcription factor, which can modulate HBV enhancer/promoter activity and transcription. Quasdorff, M. et al. *Journal of viral hepatitis* 17, 527-536 (2010), Bar-Yishay, I., et al. *Liver international: official journal of the International Association for the Study of the Liver* 31, 282-290 (2011). Results obtained from an HBV enhancer/promoter reporter assay with or without miR-130a indicated that miR-130a, but not miR-204 or the vector control, reduced the luciferase activity driven by HBV enhancer-II (FIG. 3H).

MiR-130a Directly Targets at Both PGC1α and PPARγ

Four different target prediction algorithms were used to identify potential target transcription factors of miR-130a in hepatocytes. PPARGC1-α (PGC1α) was identified as such a factor whose 3'UTR was consistently predicted by all four programs (Table 4).

TABLE 4

Prediction of miR-130a target sites at the 3'UTR of human transcription factors known to influence HBV transcription

| Transcription factors £ | Target scan | PicTar | DIANA | RNAhybrid |
|---|---|---|---|---|
| HNF1 | + | − | − | − |
| HNF4α | + | − | − | − |
| C/EBPα | − | − | − | − |
| C/EBPβ | − | − | − | − |

TABLE 4-continued

Prediction of miR-130a target sites at the 3'UTR of human transcription factors known to influence HBV transcription

| Transcription factors £ | Target scan | PicTar | DIANA | RNAhybrid |
|---|---|---|---|---|
| SP1 | + | − | + | − |
| RXRα | + | − | + | − |
| PPARα | + | − | − | − |
| PPARγ | + | − | − | + |
| FoxA3 (HNF3γ) | − | − | − | − |
| FoxO1 | − | − | − | − |
| FXRα | − | − | − | − |
| PGC1α | + | + | + | + |
| ERRα | − | − | − | − |
| COUP-TF | − | − | − | − |
| LRH | − | − | − | − |

£ These transcription factors had been reported to be involved in HBV RNA synthesis in literatures5, 6, 38. MiR-130a was shown to target at the 3' UTR of PPARγ in adipocytes. Lee, E. K. et al. *Mol Cell Biol* 31, 626-638 (2011).

To address the potential relationship between miR-130a and PGC1α, a stable cell lines expressing miR-130a was established (FIG. 3I). While the expression levels of most hepatic transcription factors being examined here remained unchanged in miR-130a expressing cell lines, simultaneous reductions of PPARγ and PGC1α mRNAs and proteins were observed (FIG. 3J, 3K; FIG. 3L), suggesting that miR-130a can target both PPARγ and PGC1α. In a reciprocal experiment, HepG2 cells were treated with LNA-miR-130a antagomir, and an increase of PGC1α mRNA and protein was observed (FIG. 3M). Therefore, miR-130a may reduce PPARγ and PGC1α protein levels (FIG. 3K) by reducing their respective mRNA levels (FIG. 3J, 3M).

To distinguish between a direct and an indirect mechanism of miR-130a on reducing PGC1α mRNA, a reporter assay was performed using 3'UTR from either PPARγ or PGC1α. The results support a functional interaction between miR-130a and the 3' UTR of PPARγ or PGC1α (FIG. 3N). Next, compensatory mutations were introduced into the seed sequences of miR-130a and its evolutionarily conserved target site of PGC1α (FIG. 3O). By cotransfection assay, only the combination of a mutant miR-130a and a mutant PGC1α could successfully restore the inhibitory effect of miR-130a on the luciferase activity. In a dose-dependent manner, miR-130a could reduce, while LNA-miR-130a could increase, the luciferase activity of a reporter containing the 3'UTR of PGC1α (FIG. 3P). Taken together, miR-130a can directly target at both PGC1α and PPARγ.

PGC1α Promote HBV DNA Replication and Protein Expression

The relationship between HBV and PGC1α was investigated by cotransfecting HBV genome with either PGC1α siRNA or PGC1α expression vector (FIGS. 3Q, 3R, 3S, 3T, 3U, 3V, 3W and 3X). The results confirm that PGC1α may stimulate HBV replication. Shlomai, A., et al. *Proceedings of the National Academy of Sciences of the United States of America* 103, 16003-16008 (2006), Ondracek, C. R., et al. *Journal of virology* 83, 12535-12544 (2009).

Synergistic Effect of PPARγ and PGC1α on Enhancing HBV DNA Replication

It remains controversial whether PPARγ (or its agonists) has a positive or negative effect on HBV replication. Yu, X. et al. *Journal of virology* 75, 11354-11364 (2001), Wakui, Y. et al. *Biochemical and biophysical research communications* 396, 508-514 (2010), Yoon, S. et al. *Virology* 409, 290-298 (2011). By increasing the concentration of a PPARγ agonist (Rosiglitazone), increasing HBV replication was observed (FIG. 3Y). In contrast, when PPARγ antagonist (GW9662) was increased in concentration, HBV replication and protein expression were significantly reduced (FIGS. 3Y and 3Z). Interestingly, the combination of both PPARγ and PGC1α, in the absence of any exogenous ligands exhibited a dramatic synergistic effect on HBV replication (FIG. 4A), and secretions of HBsAg, HBeAg (FIG. 4B). Cotransfection of HBV ayw dimer with the combination of both PGC1α and PPARγ siRNAs resulted in the most potent inhibitory effect on HBV DNA replication (FIG. 4D) and expression of HBsAg and HBeAg (FIG. 4E). FIG. 4C summarized a preliminary triad relationship among HBV, miR-130a, PPARγ and PGC1α. In this diagram, miR-130a can indirectly attenuate HBV replication and expression by dual targeting at both PPARγ and PGC1α, which have a synergistic positive effect on HBV replication.

MiR-130a in Hepatic Gluconeogenesis and Lipogenesis

The dual targets of PGC1α and PPARγ by miR-130a strongly suggest its important role in energy metabolism. Several key metabolic enzymes in glycolysis, gluconeogenesis, and lipogenesis were examined using stable miR-130a expressing cells (FIG. 5A, upper panel). Both phosphoenolpyruvate carboxykinase (PEPCK) and glucose-6-phosphatase (G6Pase) are rate-limiting gluconeogenic enzymes known to be under the positive control of PGC1α, Yoon, J. C. et al. *Nature* 413, 131-138 (2001). Since PGC1α mRNA and proteins were reduced in miR-130a expressing cells (FIG. 3J, 3K), it was anticipated that PEPCK and G6Pase should be reduced as well. Indeed, concurrent reductions of PEPCK and G6Pase mRNAs (FIG. 5A) and proteins (FIG. 5B) were observed in miR-130a expressing hepatocytes. While this result suggested a glycolysis rather than a gluconeogenesis pathway, it would be more certain if their glycolytic counterparts, pyruvate kinase (PKLR) and glucokinase (GCK), was not reduced simultaneously (FIG. 5A). Indeed, the protein expression of GCK and PLKR was not reduced but increased in HepG2 or Huh7 cells (FIG. 5B). Furthermore, increased mRNA expression of both GCK and PLKR was observed in miR-130a expressing hepatocytes (FIGS. 5C and 5D). These results suggest that miR-130a can not only inhibit HBV replication, but also contribute to downregulation of gluconeogenesis and upregulation of glycolysis in hepatocytes via PGC1α. Thus, miR-130a would be effective in diseases and disorders associated with dysregulation of glycolysis, such as metabolic diseases.

A Metabolic Triad

HBV may exert any effect on PGC1α and PPARγ. Consistent with the reduction of miR-130a (FIG. 1A, Table 2), PGC1α, PEPCK, G6Pase and PPARγ proteins were all significantly increased in HBV-producing UP7-4 and UP7-7 cells (FIG. 5E). Similarly, glucose production was increased in stable PGC1α-producing cells, and decreased in PPARγ-producing cells (FIG. 5F). No significant difference in glucose level was detected between control and miR-130a producing cells. The glucose level was increased in HBV-producing HepG2 cells, and further increased when HepG2 cells were treated with a PPARγ antagonist, GW9662, irrespective of its HBV-producing status (FIG. 5G). Finally, there was no apparent change in miR-130a expression in stable PGC1α-expressing cell lines (FIG. 5H).

A triad relationship among HBV, miR-130a, and PGC1α is outlined in FIG. 5I. In contrast to PGC1α, expression of miR-130a was reduced in stable PPARγ-expressing cell line, and further reduced by Rosiglitazone treatment, but not by GW9662 (FIG. 5J). Furthermore, combination of PGC1α and PPARγ, in the absence of any exogenous ligands, exhibited an even stronger effect on reducing miR-130a expression than PGC1α or PPARγ alone (FIG. 5K). These results suggest another triad diagram with a positive feed-forward loop (FIG. 5L). A primary weak signal received by this loop may be amplified into a stronger phenotypic outcome.

HBV-Transgenic Mice Exhibited Reduced Levels of miR-130a and miR-204

The effect of miR-130a and miR-204 on HBV infection was explored using HBV transgenic mice, Chen, C. C. et al. *Gene therapy* 14, 11-19 (2007), whose liver contains active HBV replication (FIG. 5M). In this animal model, hepatic miR-130a and miR-204 was significantly reduced (FIG. 5N) and HBc was strongly expressed, while PGC1α, G6Pase, PEPCK, and PPARγ were all significantly increased (FIG. 5P). Unlike the cell culture system (FIG. 5G), no significant difference in serum glucose levels was detected between wild type and HBV-transgenic mice (FIG. 5O; see Discussion). In this animal model, hepatic miR-130a (FIG. 5N) and NF-κB/p65 (FIG. 5P) were significantly reduced, while HBc was strongly expressed. Similarly, PGC1α, G6Pase, PEPCK, PPARγ were all significantly increased (FIG. 5P).

Mir-204 can Inhibit HBV pgRNA Packaging and Capsid Assembly

It was observed in this study that miR-204 could reduce HBV DNA replication without any apparent reduction in HBV specific RNA and proteins (FIGS. 1 and 2C). This may due to the activity of miR-204 in interfering with HBV capsid assembly, RNA encapsidation, or reverse transcription (FIG. 6A). Following cotransfection with HBV DNA and miR-204 expression vector, the assembly efficiency and stability of intracellular core particles were examined by native agarose gel electrophoresis (FIG. 6B, upper panel), Newman, M., et al. *Journal of virology* 83, 10616-10626 (2009), Chua, P. K., et al. *Journal of virology* 84, 2340-2351 (2010). As a control, the level of core protein was monitored by denaturing SDS-PAGE (FIG. 6B, lower panel). Cotransfection with miR-204 significantly reduced the level of intracellular core particles in HepG2 cells, while the total amount of core protein monomer remained unchanged. This result suggests that miR-204 interferes with HBV capsid assembly. HBV replicates via reverse transcription of an encapsidated RNA pregenome, Summers, J. et al. *Cell* 29, 403-415 (1982).

Encapsidated RNA or polyanions can induce capsid assembly, Newman, M., et al. *Journal of virology* 83, 10616-10626 (2009), Chua, P. K., et al. *Journal of virology* 84, 2340-2351 (2010). The efficiencies of pgRNA encapsidation with and without miR-204 were compared by ribonuclease protection assay (RPA) of core particle-associated HBV RNA (FIG. 6C). Cotransfection with miR-204 reduced core particle-associated RNA, without any apparent effect on total cytoplasmic viral RNA. Our results suggest that miR-204 targets a host factor involved in capsid assembly or RNA encapsidation.

Regulation of miR-130a

One important issue to address here is how the expression of miR-130a can be regulated. Bioinformatic analysis revealed three potential binding sites for transcription factors NF-κB/p65, Egr-1, and CREB, at 1000 nt upstream from the transcription start site (FIG. 7A). A promoter assay of miR-130a was conducted using a luciferase reporter (FIG. 7B). When the binding site of NF-κB/p65 is deleted, luciferase activity is significantly reduced. This result strongly suggests that NF-κB/p65 is a positive activator for miR-130a transcription. Indeed, when rat or mouse NF-κB/p65 expression vector was cotransfected with the miR-130a promoter plasmid, a 30-60 fold increase of luciferase activity was observed (FIG. 7C). Conversely, siRNA treatment specific for NF-κB/p65 significantly reduced the level of miR-130a in transfected HepG2 cells by stem-loop PCR measurement (FIG. 7D). It has been reported that PPARγ can serve as an E3 ligase for NF-κB/p65 ubiquitination and degradation (Ruan et al. 2003; Pascual et al. 2005; Hou et al. 2012). Indeed, significant reduction in NF-κB/p65 protein level was observed in stable PPARγ expressing HepG2 cells by Western blot analysis (FIG. 7E). Interestingly, the NF-κB/p65 protein level was increased significantly in stable miR-130a expressing HepG2 cells, a result consistent with the fact that miR-130a can target PPARγ (FIGS. 3J and 3K). The negative effect of PPARγ on NF-κB/p65 is not by targeting at the mRNA level of NF-κB/p65 by qPCR analysis (FIG. 7F). The effect of HBV on the protein level of NF-κB/p65 was investigated in HBV-producing cell line (FIG. 7G). Both phosphorylated and total NF-κB/p65 proteins were significantly reduced in the presence of HBV replication by Western blot analysis. Again, these results are consistent with the effect of PPARγ on NF-κB/p65 via protein ubiquitination and degradation (Hou et al. 2012). Consistent with this result, when HBV-producing stable cell lines UP7-4 and UP7-7 were treated with siRNA specific for PPARγ, both NF-κB/p65 and miR-130a were increased (FIG. 7H). Taken together, another feed-forward loop between miR-130a and NF-κB/p65 via PPARγ was proposed (FIG. 7I).

Discussion

A number of anti-hepatitis virus cellular microRNAs were identified in this study as being capable of attenuating, e.g., HBV replication by interference at different steps in HBV life cycle. As described in detail in the text, miR-1236 inhibits HBV replication directly, while miR-130a and miR-204 inhibits HBV indirectly. In the presence of HBV, the expression of miR-1236, miR-130a, and miR-204 is reduced, creating a more friendly niche for the hepatotropic HBV. A potential role of miR-130a in energy metabolism is discussed in the text. Treatment with combinations of oligonucleotide mimetics of these three microRNAs resulted in striking reduction of HBV replication (FIGS. 9A and 9B). These three microRNAs can inhibit the replication of HBV of different genotypes, indicating that they may be therapeutically effective in treating HBV infection. Pedersen, I. M. et al. *Nature* 449, 919-922 (2007).

The most salient feature of miR-130a is its dual targets at PPARγ and PGC1α (FIG. 3J-3N), leading to reduced HBV replication (FIG. 1B, 4A). Conversely, HBV can reduce the expression of miR-130a (Table 2, FIG. 1A), leading to increased expression of PPARγ and PGC1α (PEPCK and G6Pase). Overexpression of PPARγ reduced the level of miR-130a, and further reduction of miR-130a was observed by Rosiglitazone (FIG. 5J) or the combination of PPARγ and PGC1α (FIG. 5K). Taken together, a positive feed-forward loop among HBV, miR-130a, PGC1α and PPARγ, was established (FIG. 5L). This triad loop could in theory magnify a weak primary signal by going through this loop repetitive rounds.

Unlike HCV, Mason, A. L. et al. *Hepatology* 29, 328-333 (1999), Mehta, S. H. et al. *Ann Intern Med* 133, 592-599 (2000), chronic hepatitis B patients do not have higher prevalence of T2DM, Mehta, S. H. et al. *Ann Intern Med* 133, 592-599 (2000), Huang, Z. S. et al. *J Gastroenterol Hepatol* 25, 1420-1425 (2010). In the presence of HBV, miR-130a level was reduced (Table 2, FIG. 1A), leading to increased PGC1α and gluconeogenesis, and perhaps in the long run, also increased the risk to T2DM. However, a reduced amount of miR-130a in HBV-producing hepatpcytes can also promote the expression of PPARγ. Therefore HBV may have evolved a strategy to down-regulate the expression of miR-130a, and thus benefit itself by creating a niche with more abundant PGC1α and PPARγ.

In the presence of HBV, the level of miR-130a was reduced, probably due to a reduced level of NF-κB/p65 in hepatocytes. Since miR-130a can target both PGC1α and PPARγ mRNAs simultaneously, the reduction of miR-130a can result in elevated levels of PGC1α and PPARγ, which can coactivate HBV transcription, leading to increased HBV DNA replication. It has been reported previously that PPARγ protein can serve as an E3 ligase for NF-κB/p65, resulting in NF-κB/p65 protein ubiquitination and degradation, leading to the reduction of NF-κB/p65 and miR-130a promoter activity. HBV can create a more friendly niche for itself by reducing the level of miR-130a via a positive feed-forward loop. Metabolically, PGC1α is known to be a positive transcriptional coactivator of hepatic gluconeogenesis. PPARγ is a positive transcription factor for lipogenesis which in turn can reduce blood glucose level. By dual targeting at PGC1α and PPARγ, miR-130a could play a critical role in glucose homeostasis. Liver inflammation could favor viral clearance (FIG. 8A), since when NF-κB and miR-130a are elevated, PGC1α, PPARγ and HBV replication are reduced. In contrast, when liver is without inflammation, the levels of both NF-κB and miR-130a are low, and the levels of PGC1α and PPARγ are higher, resulting in more active viral replication.

Example 2: Regulating HCV Replication by miR-130a

It has been well documented that chronic HCV infection is associated with a higher incidence of type 2 diabetes mellitus (T2DM) (Huang et al., 2007; Mason et al., 1999; Mehta et al., 2000). The regulatory role of miR-130a in HCV infection was explored as follows.

HCV genotype 2a chimeric construct FL-J6/JFH1 plasmid DNA was linearized with XbaI restriction enzyme and extracted by phenol/chloroform. The purified DNA was used as the template for HCV RNA in vitro transcription using T7 MEGAscript kit (Ambion) according to the manufacturer's instruction. For electroporation, subconfluent Huh7.5 cells were detached by trypsin, collected by centrifugation (1000 g, 5 mins) and resuspended at $1.5 \times 10^7$ cells/mL in ice-cold phosphate-buffered saline. A 400 μL aliquot of cells was then mixed with 10 μg of HCV RNA in a 4 mm gap cuvette. Electroporation condition was 3 pulses of 300 volts for 500 microseconds with 1.1 second intervals using an ECM830 (BTX) electroporator. Following a 10-minute recovery time, cells were diluted in complete DMEM medium for HCV supernatant collection at day 3~7 post electroporation. HCV-containing supernatant was clarified by centrifugation (1,500×g) for 10 min and filtered through a 0.22 μM filter. Virus was concentrated by addition of one-fourth volume sterile 40% (w/v) polyethylene glycol-8000 in PBS (final, 8% (w/v)) and overnight incubation at 4 C. Virus precipitates were collected by centrifugation (4,000×g, 45 min) and resuspended in DMEM. For longer term storage, HCV aliquots were stored at −80° C. After 2 hour infection, virus was removed from the cells and replaced with fresh complete DMEM medium. Infected cells were collected at different time points for protein and RNA extraction. For virus titration, culture supernatants were 10-fold serially diluted in complete DMEM and used to infect $4 \times 10^3$ naïve Huh7.5 cells per well in 96-well plates. The inoculum was incubated with cells for 2 h at 37° C. and then supplemented with fresh complete DMEM. The level of HCV infection was determined 2 day post-infection by immunofluorescence microscopy using anti-HCV NS5A antibody (9E10). The virus titer was expressed in focus-forming units/ml supernatant (f.f.u./ml), as determined by the mean number of HCV-positive foci detected at the highest dilutions.

The time course of miR-130a expression profiles in HCV-infected Huh7 and Huh7.5 cells were examined. As shown in FIGS. 10A-D, miR-130a was reduced in human hepatoma Huh7 and Huh7.5 cells upon in vitro infection with HCV. On day 1 post-infection with HCV, miR-130a was reduced. However, miR-130a levels were gradually restored over time to a pre-infection (i.e., un-infected) level. These data suggest that miR-130a is important for the establishment of HCV infection initially (day 1), before establishment of stable infection. Thus, modulating miR-130a or the related miR-130b might be effective in regulating HCV replication and treating HCV infection.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of inhibiting replication of hepatitis B virus (HBV), the method comprising contacting liver cells infected with HBV with a miR-130a RNA, a miR-130b RNA, a miR-204 RNA, a miR-1236 RNA, or a combination thereof in an amount effective for inhibiting replication of the HBV, whereby HBV replication in the liver cells is inhibited.

2. The method of claim 1, wherein the liver cells are contacted with the miR-130a RNA or the miR-130b RNA in an amount effective to reduce PGC1α, PGC1β, or PPARγ.

3. The method of claim 1, wherein the liver cells are contacted with the miR-1236 in an amount effective to reduce the level of hepatitis B virus-encoded RNA.

4. The method of claim 1, wherein the liver cells are contacted with the miR-204 RNA in an amount effective to inhibit HBV pregenomic RNA encapsidation, capsid assembly, or both.

5. The method of claim 1, wherein the miR-130a RNA, the miR-130b RNA, the miR-204 RNA, or the miR-1236 RNA is a duplex RNA molecule, a single-strand RNA molecule, or is encoded by an expression vector.

6. The method of claim 1, wherein the liver cells are contacted with a combination of the miR-130a RNA, the miR-204 RNA, and the miR-1236 RNA, or a combination of the miR-130b RNA, the miR-204 RNA, and the miR-1236 RNA.

7. The method of claim 1, wherein the contacting step is performed by administering to a subject in need thereof an effective amount of the miR-130a RNA, the miR-130b RNA, the miR-204 RNA, the miR-1236 RNA, or a combination thereof.

8. The method of claim 7, wherein the miR-130a RNA contains the nucleotide sequence of CAGUGCAAUGUUAAAAGGGCAU (SEQ ID NO:1).

9. The method of claim 7, wherein the miR-130b RNA contains the nucleotide sequence of CAGUGCAAUGAUGAAAGGGCAU (SEQ ID NO:2).

10. The method of claim 7, wherein the miR-204 RNA contains the nucleotide sequence of UUCCCUUUGUCAUCCUAUGCCU (SEQ ID NO:3).

11. The method of claim 7, wherein the miR-1236 RNA contains the nucleotide sequence of CCUCUUCCCCUUGUCUCUCCAG (SEQ ID NO:4).

12. The method of claim 7, wherein the subject is a human patient having an HBV infection.

13. The method of claim 12, further comprising administering to the subject an effective amount of an anti-HBV agent that is not the miR-130a RNA, miR-130b RNA, miR-204 RNA, or miR-1236 RNA.

14. The method of claim 1, wherein the liver cells are cultured cells infected with HBV.

15. The method of claim 14, wherein the miR-130a RNA contains the nucleotide sequence of CAGUGCAAUGUUAAAAGGGCAU (SEQ ID NO:1).

16. The method of claim 14, wherein the miR-130b RNA contains the nucleotide sequence of CAGUGCAAUGAUGAAAGGGCAU (SEQ ID NO:2).

17. The method of claim 14, wherein the miR-204 RNA contains the nucleotide sequence of UUCCCUUUGUCAUCCUAUGCCU (SEQ ID NO:3).

18. The method of claim 14, wherein the miR-1236 RNA contains the nucleotide sequence of CCUCUUCCCCUUGUCUCUCCAG (SEQ ID NO:4).

* * * * *